United States Patent
Geddes

(10) Patent No.: US 10,379,050 B2
(45) Date of Patent: Aug. 13, 2019

(54) SPECTRAL SHIFTS AND MODIFICATIONS IN METAL-ENHANCED FLUORESCENCE, PHOSPHORESCENCE AND ALPHA-FLUORESCENCE

(71) Applicant: UNIVERSITY OF MARYLAND, BALTIMORE COUNTY, Baltimore, MD (US)

(72) Inventor: Chris D. Geddes, Bel-Air, MD (US)

(73) Assignee: UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 441 days.

(21) Appl. No.: 14/994,513

(22) Filed: Jan. 13, 2016

(65) Prior Publication Data

US 2016/0202183 A1  Jul. 14, 2016

Related U.S. Application Data

(60) Provisional application No. 62/102,866, filed on Jan. 13, 2015.

(51) Int. Cl.
*G01N 33/553* (2006.01)
*G01N 21/64* (2006.01)
*G01N 33/50* (2006.01)

(52) U.S. Cl.
CPC ....... *G01N 21/648* (2013.01); *G01N 21/6428* (2013.01); *G01N 33/553* (2013.01); *G01N 33/50* (2013.01); *G01N 2021/6439* (2013.01)

(58) Field of Classification Search
CPC ............. G01N 21/6428; G01N 21/648; G01N 2021/6439
See application file for complete search history.

(56) References Cited

U.S. PATENT DOCUMENTS

| | | | |
|---|---|---|---|
| 5,376,556 A * | 12/1994 | Tarcha | G01N 21/658 435/968 |
| 5,939,021 A * | 8/1999 | Hansen | C12Q 1/6816 422/400 |
| 6,297,059 B1 * | 10/2001 | Song | G01N 33/542 436/501 |
| 7,095,502 B2 | 8/2006 | Lakowicz et al. | |
| 7,400,397 B2 | 7/2008 | Lakowicz et al. | |
| 7,566,783 B2 | 7/2009 | Lakowicz et al. | |
| 7,718,804 B2 | 5/2010 | Geddes et al. | |
| 7,732,215 B2 | 6/2010 | Geddes et al. | |
| 7,776,528 B2 | 8/2010 | Lakowicz | |
| 7,939,333 B2 | 5/2011 | Geddes et al. | |
| 7,989,220 B2 | 8/2011 | Lakowicz et al. | |
| 8,008,067 B2 | 8/2011 | Geddes et al. | |
| 8,027,039 B2 | 9/2011 | Lakowicz et al. | |
| 8,034,633 B2 | 10/2011 | Geddes | |
| 8,075,956 B2 | 12/2011 | Geddes et al. | |
| 8,101,424 B2 | 1/2012 | Geddes | |
| 8,114,598 B2 | 2/2012 | Geddes et al. | |
| 8,182,878 B2 | 5/2012 | Geddes et al. | |
| 8,318,087 B2 | 11/2012 | Geddes | |
| 8,338,602 B2 | 12/2012 | Geddes et al. | |
| 8,404,450 B2 | 3/2013 | Geddes et al. | |
| 8,569,502 B2 | 10/2013 | Geddes et al. | |
| 8,618,505 B2 | 12/2013 | Geddes | |
| 8,679,402 B2 | 3/2014 | Geddes | |
| 8,679,855 B2 | 3/2014 | Geddes | |
| 8,722,428 B2 | 5/2014 | Geddes | |
| 8,735,175 B2 | 5/2014 | Geddes | |
| 8,759,110 B2 | 6/2014 | Geddes | |
| 9,075,018 B2 | 7/2015 | Geddes et al. | |
| 9,170,197 B2 | 10/2015 | Geddes et al. | |
| 9,244,012 B2 * | 1/2016 | Geddes | G01N 21/64 |
| 2001/0029049 A1 * | 10/2001 | Walt | G01N 21/6428 436/518 |
| 2002/0135771 A1 * | 9/2002 | Witty | G01N 33/558 356/445 |
| 2002/0141999 A1 * | 10/2002 | Lyman | C07K 14/4702 424/178.1 |
| 2002/0150938 A1 * | 10/2002 | Kneipp | C12Q 1/6816 435/6.11 |
| 2003/0077660 A1 * | 4/2003 | Pien | B01L 3/5085 435/7.1 |

(Continued)

FOREIGN PATENT DOCUMENTS

WO  WO2004024191  3/2004
WO  WO2007095527  8/2007

OTHER PUBLICATIONS

C. D. Geddes, "Metal-enhanced Fluorescence," Phys. Chem. Chem. Phys. 15(45), (2013), pp. 19521-19940.
N. Sui, L. Wang, T. Yan, F. Liu, J. Sui, Y. Jiang, J. Wan, M. Liu, and W. W. Yu, "Selective and sensitive biosensors based on metal-enhanced fluorescence," Sens. Actuators B 202, pp. 1148-1153, (2014).
M. Bauch, K. Toma, M. Toma, Q. Zhang, and J. Dostalek, "Plasmon-Enhanced Fluorescence Biosensors: a Review," Plasmonics 9(4), pp. 781-799, (2014).
M. Ganguly, C. Mondal, J. Chowdhury, J. Pal, A. Pal, and T. Pal, "The tuning of metal enhanced fluorescence for sensing applications," Dalton Trans. 43(3), pp. 1032-1047, (2014).
L. Zhang, Y. Song, T. Fujita, Y. Zhang, M. Chen, and T.-H. Wang, "Large Enhancement of Quantum Dot Fluorescence by Highly Scalable Nanoporous Gold," Adv. Mater. 26(8), pp. 1289-1294, (2014).

(Continued)

*Primary Examiner* — Christopher L Chin
(74) *Attorney, Agent, or Firm* — Tristan A. Fuierer; Marianna Fuierer; Olive Law Group, PLLC

(57) ABSTRACT

The present invention provides for excitable molecules positioned near metallic structures, wherein the metallic structures have a particles size from about 1 nm to 1000 nm and wherein the excitable molecules have fluorescence, phosphorescence or alpha-fluorescence emissions that are altered due to positioning near the metal structures. The emission spectra are distorted on either the blue or red edges in a range from 1 to 10 nm thereby changing the color of emissions. Further, the width of the emission spectrum is modified either by narrowing or broadening depending on the material of the metallic structures and type of excitable molecule.

10 Claims, 19 Drawing Sheets

(56) References Cited

U.S. PATENT DOCUMENTS

| | | | |
|---|---|---|---|
| 2003/0143757 A1* | 7/2003 | Moore | G01N 33/53 436/518 |
| 2003/0228682 A1 | 12/2003 | Lakowicz | |
| 2004/0186359 A1* | 9/2004 | Beaudoin | A61B 5/0075 600/310 |
| 2005/0196876 A1* | 9/2005 | Chan | G01N 21/65 436/518 |
| 2006/0256331 A1 | 11/2006 | Geddes | |
| 2007/0269826 A1 | 11/2007 | Geddes | |
| 2008/0215122 A1 | 9/2008 | Geddes | |
| 2009/0022766 A1 | 1/2009 | Geddes | |
| 2009/0325199 A1 | 12/2009 | Geddes | |
| 2011/0020946 A1 | 1/2011 | Geddes | |
| 2011/0207236 A1 | 8/2011 | Geddes | |
| 2012/0021443 A1 | 1/2012 | Geddes | |
| 2012/0028270 A1 | 2/2012 | Geddes | |
| 2012/0107952 A1 | 5/2012 | Geddes | |
| 2012/0282630 A1 | 11/2012 | Geddes | |
| 2013/0115710 A1 | 5/2013 | Geddes | |
| 2013/0156938 A1 | 6/2013 | Geddes | |

OTHER PUBLICATIONS

Y. Zhang, K. Aslan, M. J. R. Previte, and C. D. Geddes, "Metal-enhanced fluorescence from copper substrates," Appl. Phys. Lett. 90(17), 173116 (2007); doi 10.1063/1.2732185.

M. H. Chowdhury, K. Ray, S. K. Gray, J. Pond, and J. R. Lakowicz, "Aluminum Nanoparticles as Substrates for Metal-Enhanced Fluorescence in the Ultraviolet for the Label-Free Detection of Biomolecules," Anal. Chem. 81(4), pp. 1397-1403, (2009).

K. Aslan, M. J. R. Previte, Y. Zhang, and C. D. Geddes, "Metal-Enhanced Fluorescence from Nanoparticulate Zinc Films," J. Phys. Chem. C 112(47), pp. 18368-18375, (2008).

R. Matsumoto, H. Yonemura, and S. Yamada, "Photoelectrochemical Responses from Zinc Porphyrin-Silver Nanoparticle Composite Films Fabricated on ITO Electrodes," J. Phys. Chem. C 117(6), pp. 2486-2493 (2013); Abstract Only.

X. Zhang, L. Fu, J. Liu, Y. Kuang, L. Luo, D. G. Evans, and X. Sun, "Ag@zinc-tetraphenylporphyrin core-shell nanostructures with unusual thickness-tunable fluorescence," Chem. Commun. 49(34), pp. 3513-3515, (2013).

J. Karolin and C. Geddes, "Spectral shifts in metal-enhanced fluorescence," Appl. Phys. Lett. 105(6), 063102 (2014); doi: 10.1063/1.48922925.

E. C. Le Ru, P. G. Etchegoin, J. Grand, N. Félidj, J. Aubard, and G. Lévi, "Mechanisms of Spectral Profile Modification in Surface-Enhanced Fluorescence," J. Phys. Chem. C 111(44), pp. 16076-16079; (2007); Abstract Only.

E. C. Le Ru , J. Grand , N. Félidj , J. Aubard , G. Lévi , A. Hohenau, J. R. Krenn , E. Blackie , and P. G. Etchegoin , in "Metal-Enhanced Fluorescence," edited by C. D. Geddes ( John Wiley & Sons, Inc., 2010), pp. 25-65; Abstract Only.

A. I. Dragan and C. D. Geddes, "Metal-enhanced fluorescence: The role of quantum yield, Q(0), in enhanced fluorescence," Appl. Phys. Lett. 100, 093115 (2012); doiL 10.1063/1.3692105.

C. D. Geddes , "Metal-Enhanced Fluorescence" ( Wiley-Blackwell, Oxford, 2010); Abstract Only.

C. D. Geddes and M. H. Chowdhury, "Plasmonics special issue—Advances in metal-molecular interactions," Plasmonics 2, 95 (2007); Cannot Locate Reference; doi: 10.1007/511468-007-9042-y.

N. Mauser and A. Hartschuh , "Tip-enhanced near-field optical microscopy," Chem. Soc. Rev. 43, 1248-1262.

Y. X. Zhang, B. L. Mali, C. Aitken, and C. D. Geddes, "Highly sensitive quantitation of human serum albumin in clinical samples for hypoproteinemia using metal-enhanced fluorescence," J. Fluoresc. 23, 187-192 (2013).

A. I. Dragan, M. T. Albrecht, R. Pavlovic, A. M. Keane-Myers and C. D. Geddes, "Ultra-fast pg/ml anthrax toxin (protective antigen) detection assay based on microwave-accelerated metal-enhanced fluorescence," Anal. Biochem. 425, 54-61 (2012).

S. M. Tennant, Y. X. Zhang, J. E. Galen, C. D. Geddes, and M. M. Levine, "Ultra-fast and sensitive detection of non-typhoidal *Salmonella* using microwave-accelerated metal-enhanced fluorescence ("MAMEF")," PLoS One 6, e18700 (2011); doiL 10.1371/journal.pone.0018700.

G. H. Chan, J. Zhao, E. M. Hicks, G. C. Schatz, and R. P. Van Duyne, "Plasmonic properties of copper nanoparticles fabricated by nanosphere lithography," Nano Lett. 7, 1947-1952 (2007).

K. Sugawa, T. Tamura, H. Tahara, D. Yamaguchi, T. Akiyama, J. Otsuki, Y. Kusaka, N. Fukuda, and H. Ushijima, "Metal-enhanced fluorescence platforms based on plasmonic ordered copper arrays: Wavelength dependence of quenching and enhancement effects," ACS Nano 7, 9997-10010 (2013); Abstract Only.

A. I. Dragan, B. Mali, and C. D. Geddes, " Wavelength-dependent metal-enhanced fluorescence using synchronous spectral analysis," Chem. Phys. Lett 556, 168-172 (2013).

A. I. Dragan and C. D. Geddes, "Excitation volumetric effects (EVE) in metal-enhanced fluorescence," Phys. Chem. Chem. Phys. 13, 3831-3838 (2011).

K. Aslan, I. Gryczynski, J. Malicka, E. Matveeva, J. R. Lakowicz, and C. D. Geddes, "Metal-enhanced fluorescence: an emerging tool in biotechnology," Curr. Opin. Biotechnol. 16(1), 55-62 (2005).

C. Geddes and J. Lakowicz, "Metal-Enhanced Fluorescence," J. Fluorescence 12(2), pp. 121-129, (2002).

K. Aslan, Z. Leonenko, J. Lakowicz, and C. Geddes, "Annealed Silver-Island Films for Applications in Metal-Enhanced Fluorescence: Interpretation in Terms of Radiating Plasmons," J. Fluorescence 15(5), pp. 643-654, (2005).

H. Hamo, J. Karolin, B. Mali, A. Kushmaro, R. Marks, and C. Geddes, "Metal-enhanced fluorescence from zinc substrates can lead to spectral distortion and a wavelength dependence," Applied Physics Letters, vol. 106, 081605 (2015); doi: 10.1063/1.4913671.

* cited by examiner

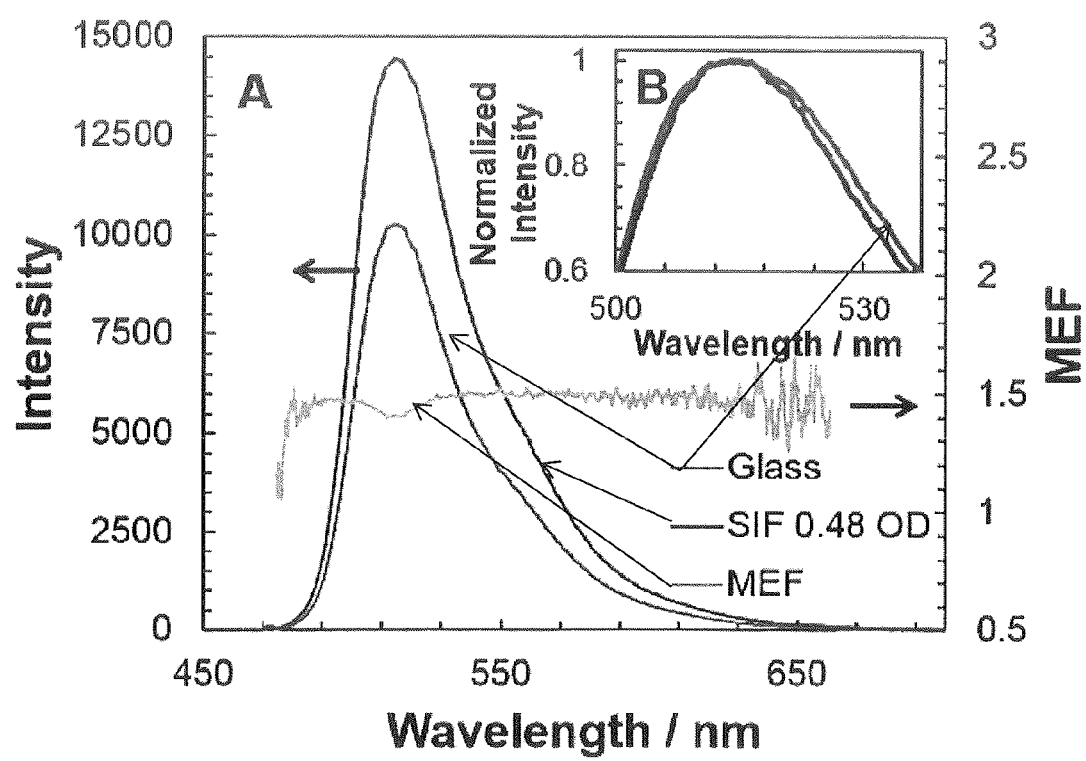
Fig. 14 A and B

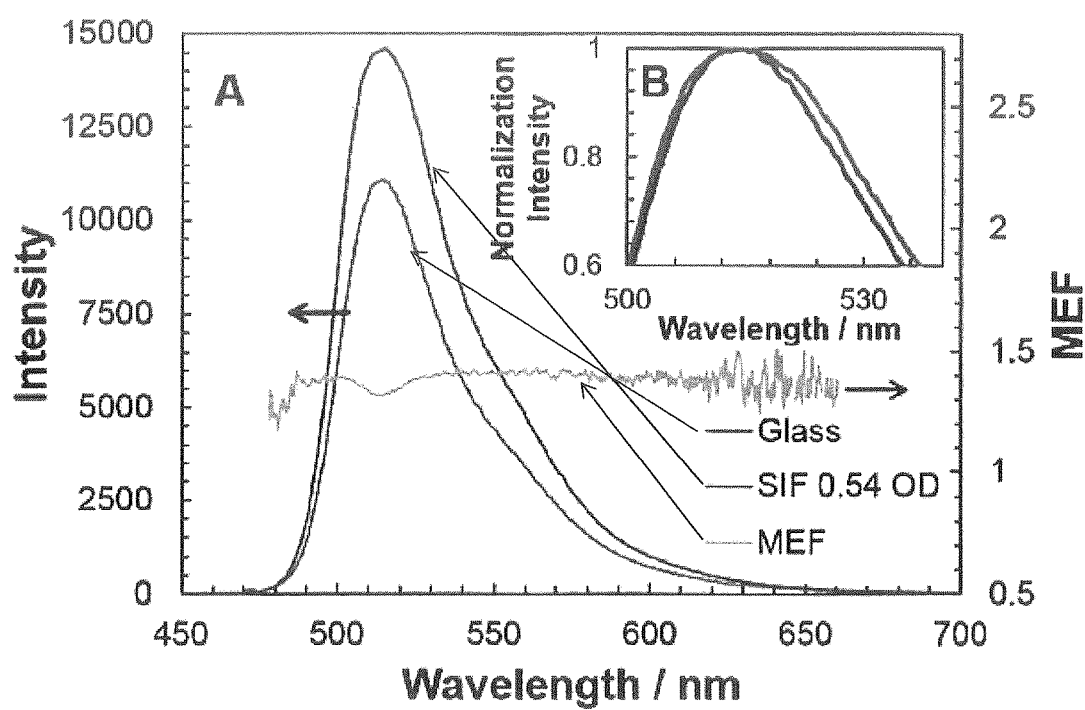
Fig. 16 A and B

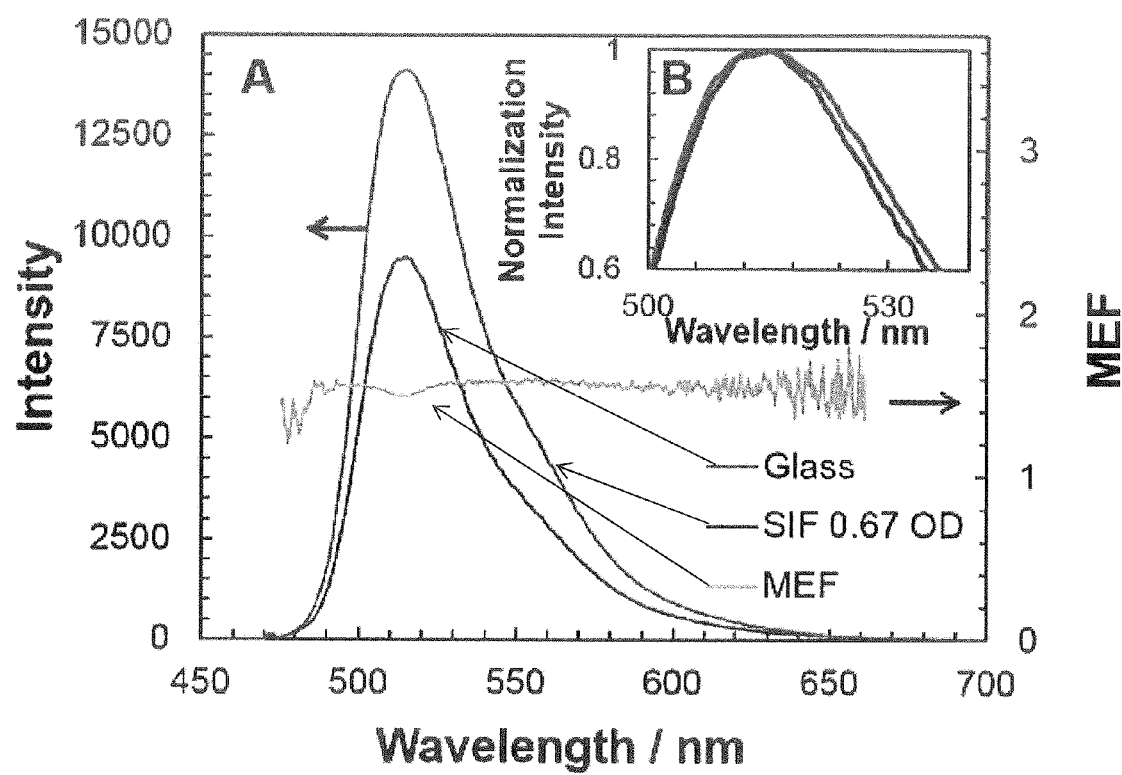
Fig. 17 A and B

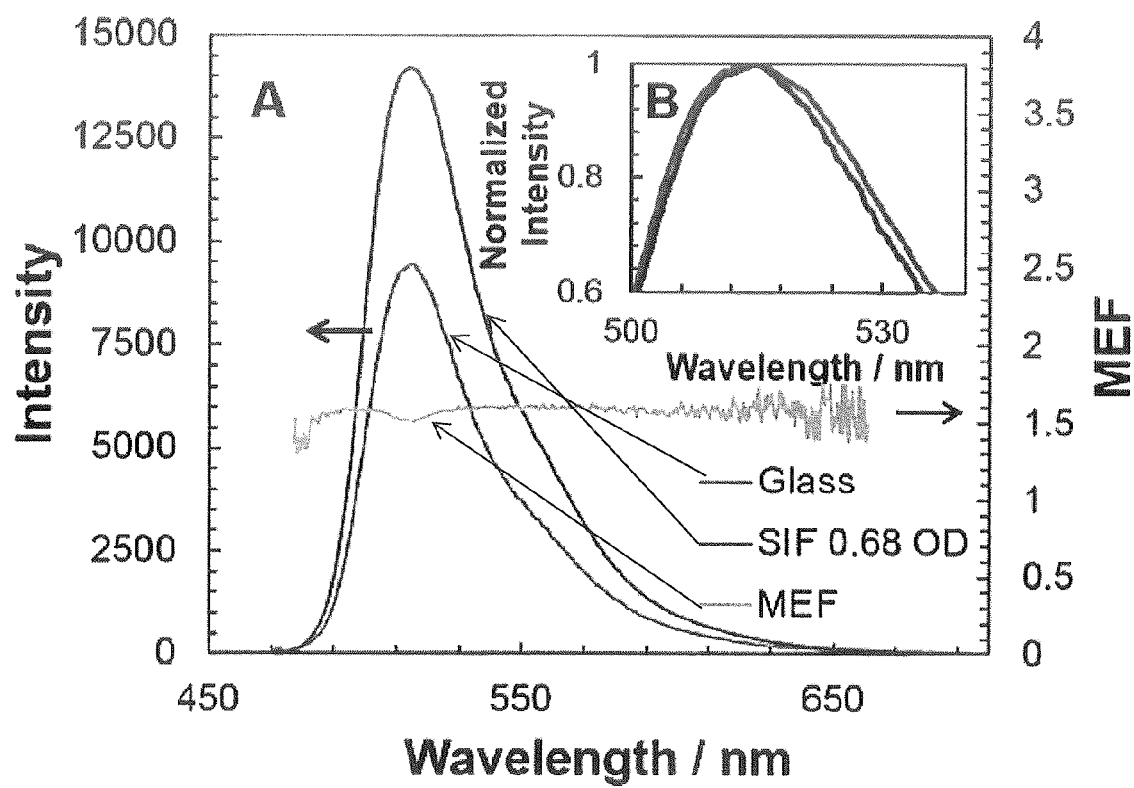
Fig. 18 A and B

SPECTRAL SHIFTS AND MODIFICATIONS IN METAL-ENHANCED FLUORESCENCE, PHOSPHORESCENCE AND ALPHA-FLUORESCENCE

CROSS-REFERENCE TO RELATED APPLICATION

This application claims priority to U.S. Provisional Patent Application No. 62/102,866 filed on Jan. 13, 2015, the contents of which is hereby incorporated by reference herein for all purposes.

BACKGROUND OF THE INVENTION

Field of Invention

The present invention relates generally to the use of metallic nanoparticles to both enhance and spectrally modify the emission of excitable molecules, such as fluorophores, that being, both the shape and width of emission spectrum thereby causing a color change in emissions from the excitable molecules.

Description of Related Art

In the last 15 years, there has been a significant literature on metal-enhanced fluorescence (MEF), (1-4) where the near-field interactions of plasmon supporting nanoparticles with fluorophores typically give rise to spectroscopically favorable properties, such as enhanced fluorescence and a much improved system photostability. Most of the reports of MEF have focused on silver, due to its visible wavelength plasmon band and the subsequent ability to enhance fluorescence in the visible spectral region. Other metals have also been used to plasmon-enhance fluorescence, including gold, (5) copper, (6) Aluminum, (7) and Zinc. (8) Gold and copper nanoparticles typically enhance fluorescence in the red to near-IR region, while Aluminum and Zinc have particular advantages in the UV and visible spectral regions. Since the report of MEF from Zinc substrates by Geddes et al., (8) there have been numerous other reports. (9,10), However, in all these reports for Zinc and indeed, all of the metals, there has been virtually no reports of spectral distortions of fluorophores. Karolin and Geddes (11) recently demonstrated experimentally spectral shifts from copper substrates with Rhodamine 800 in the red spectral region (>700 nm), but there have been no reports in the UV or visible region to date. In addition, Le Ru has theoretically predicted spectral distortions, (12,13) although the fast-coupling and coupling from non-vibronically relaxed states would ultimately lead to blue-shifted emission spectra, which has not been experimentally observed to date either.

MEF has attracted significant research interest in recent years, from both a theoretical (14) and practical perspective (15-16) From a theoretical perspective, the mechanism of MEF is still under debate, but with significant progress made in the last few years, while the practical applications of MEF are widespread, including applications in imaging, e.g., tip-enhanced near-field optical microscopy, (17) high throughput analysis, (18) sensing and in the analytical and life sciences (19-20) to name but just a few.

In the vast majority of MEF studies, no spectral shifts or "distortions" are observed, with both the MEF and control sample spectra being reported as identical. Thus it would be advantageous to determine the level and amount of spectral shifts or distortions due to the proximity of different fluorophores to a variety of different metal nanoparticles.

SUMMARY OF THE INVENTION

The present invention provides for excitable molecules positioned near metallic structures, wherein the metallic structures have a particles size from about 1 nm to 1000 nm and wherein the excitable molecules have fluorescence, phosphorescence or alpha-fluorescence emissions that are altered due to positioning near the metal structures. The emission spectra are distorted on either the blue or red edges in a range from 1 to 10 nm, preferably from about 2 to 5 nm, thereby changing the color of emissions. Further, the width of the emission spectrum is modified either by narrowing or broadening depending on the material of the metallic structures and type of excitable molecule.

The metallic structures are selected from the group consisting of Silver, Gold, Aluminium, Zinc, Rhodium, lithium Copper, Nickel, Palladium, Indium, Tin, Iron, Tungsten, Platinum and Germanium, alloys thereof or a combination thereof.

In one aspect the present invention provides a substrate comprising non-connecting metalized structures that are spatially separated, wherein the metalized structures may be fabricated to form a geometric shape such as an island, rods of different aspect ratio, sphere, triangle, square, oblong, elliptical, rectangle, or any shape that provides at least one apex area of the metallic surface. It is envisioned that the apex area includes not only pointed regions but regions with rounded edges such as found in an oblong or elliptical shape. The apex areas are preferably arranged so that one apex area is opposite from another apex area and aligned to form a reactive zone to be positioned therebetween. The distances between the apex areas may range from 0.01 mm to 5 mm, more preferably from 2 mm to about 3 mm. The thickness of the metallic geometric shaped forms ranges from 10 nm to about 1000 nm, and more preferably from about 45 nm to about 250 nm.

In one aspect, the present invention provides for a system to provide for a change in emission spectra and color of such emission spectra of an excitable molecule, the system comprising:
  a. a substrate comprising a multiplicity of metallic structures;
  b. at least one excitable molecule that is positioned near the metallic structure material in a range from about 5 nm to 50 nm, wherein the excitable molecule is selected from the group of an intrinsic fluorophore, extrinsic fluorophore, fluorescent dye, and luminophores;
  c. a source of electromagnetic energy for providing excitation energy to excite the molecule; and
  d. a detector for detecting emissions from the excited molecule and/or the metallic structure, wherein the emission spectra is modified by narrowing or broadening of the spectra and thereby changing the color of emissions.

Such change in the emission spectra or distortion thereof can be used to both amplify and "change the color" of enhanced fluorescence for applications in clothing fibers, paints, colorants, tissue staining, washing/cleaning products, such as the optical brighteners in washing powders; cosmetics, such as in hair products, creams, lipsticks, nail polish, mascara, etc.; and clinical immunoassays for the detection of analytes and antigens. One typical embodiment of the technology could be using FRET (Forster Resonance Energy Transfer) based immunoassays, where spectral distortion is used to change the extent of the donor-acceptor overlap integral for FRET-based sensing. Further the technology may be used in Super Resolution Microscopy to narrow the emission profile and reduce the excited state lifetime simultaneously.

The above system may be used to provide a method for modifying an emission spectrum of a fluorophore, enhancement of such emissions and a color change color of such emissions, the method comprising:
i. providing a surface comprising a multiplicity of metallic particles;
ii. positioning an excitable molecule, such as a fluorophore, a distance from the metallic particles, wherein the distance is sufficient to enhance intensity of emissions from the excitable molecule;
iii. providing an electromagnetic energy source for exciting the excitable molecule, wherein the spectra emission from the excitable molecule is distorted and causing a color change in such emissions from the excitable molecule.

The emission enhancement may be observed when the fluorophore is positioned about 5 nm to about 200 nm from the metallic structures. Preferable distances are about 5 nm to about 40 nm, and more preferably, 5 nm to about 20 nm from the metallic structures.

Another aspect of the invention relates to a method of enhancing emissions from fluorescence, chemiluminescence, bioluminescence, and luminescence molecules and reactions that exhibit emissions in wavelengths from UV-visible to near IR.

The present invention relates to a method of detection using plasmonic emissions from metallic surfaces caused by fluorescence, chemiluminescence or bioluminescence based reactions. These plasmonic emissions emitted from metallic surface plasmons are generated either with an external excitation or without such external excitation due to chemically induced electronically excited states. Further, the mixed metal structures may be used to enhance spectral regions were the metals themselves do not have plasmon resonance, due to the creation of new mixed metal plasmon bands.

In yet another aspect, the present invention relates to a method of metal-enhanced fluorescence sensing of a biomolecule, comprising:
a. applying mixed metallic structures to a surface used in a detection system;
b. introducing a solution containing at least one biomolecule for disposing near the metallic structures, wherein the biomolecule is capable of a chemically induced electronically excited state;
c. triggering the chemically induced electronically excited state of the biomolecule; and
d. measuring the bioluminescent or chemiluminescent intensity, change in width of emission spectrum and/or change in color emissions.

In yet another aspect, the present invention relates to a method for detecting a target molecule in a sample, the method comprising:
providing a system comprising:
a layer of immobilized metallic structures, wherein the immobilized metallic structures have attached thereto a capture biomolecular probe with an affinity for the target molecule; and a free biomolecular probe with an affinity for the target molecule, wherein the free biomolecular probe has attached thereto a fluorophore;
contacting the sample with the immobilized metallic structures and capture biomolecular probes, wherein the target molecules binds to the capture biomolecular probes; and
contacting the bound target molecule with the free biomolecular probe, wherein binding of the free biomolecular probe to the target molecule causes the fluorophore to be positioned a sufficient distance from the immobilized metallic structures to enhance fluorescence emission when excited by an irradiating source and cause a distortion or modification in emission spectrum thereby causing a change in the color of such emission.

The substrate positioned beneath the metallic structures may include glass, quartz, plastics (such as on the bottom of HTS plates, polystyrene, polycarbonate), paper, cellulose, cotton, nylon, silk, sapphire, diamond, noble metal films, wool fabrics, bank notes, indium tin oxide, ruby, metallic alloys or dielectric materials.

A still further aspect of the invention relates to a bioassay for measuring concentration of receptor-ligand binding in a test sample, the method comprising:
a. preparing metal structures of the present invention immobilized on a surface wherein the metal structures have positioned thereon a receptor molecule having affinity for a ligand of interest;
b. contacting the receptor molecule with the test sample suspected of comprising the ligand of interest, wherein the ligand of interest will bind to the receptor molecule to form a receptor-ligand complex;
c. contacting the receptor-ligand complex with a detector molecule having affinity for the ligand to form a receptor-ligand-detector complex, wherein the detector molecule comprises a first component of a bioluminescence or chemiluminescence generating system;
d. exposing the first component of the bioluminescence or chemiluminescence generating system to a trigger solution comprising a second component that will chemically react with the first component to induce a chemically electronically excited state; and
e. measuring the intensity of radiation emitted and color change in emission from exited metallic surface plasmons and/or test sample.

Preferably, the components of the bioluminescence generating system are a luciferase and a luciferin. The bioluminescence generating system may be selected from the group consisting of those isolated from the ctenophores, coelenterases, mollusca, fish, ostracods, insects, bacteria, a crustacea, annelids, and earthworms. The luciferase may be selected from the group consisting of Aequorea, Vargula, Renilla, Obelin, Porichthys, Odontosyllis, Aristostomias, Pachystomias, firefly, and bacterial systems.

In a still further aspect, the present invention relates to an assay using High Throughput Screening (HTS), the method comprising:
a. providing a well plate used in HTS systems comprising a multiplicity of wells;
b. introducing metal structures into the wells, wherein the metal structures are coupled to a binding receptor having affinity for a target molecule;
c. introducing at solution suspected of including the target molecule for binding to the binding receptor;
d. applying electromagnetic energy; and
e. measuring the emissions from the system, wherein the emission is distorted and spectrum is broadened or narrowed thereby changing the color of emissions.

In another aspect, the present invention relates to a system for detecting excitable emissions and spectrum width to determine color change of the emissions, the system comprising:
a multiplicity of metallic particles positioned on a surface substrate, wherein the metalized particles are fabricated from the same or different metals;
at least one connector molecule attached to the metallic particles or near the metallized particles for binding or capture of desired molecules in a testing sample, wherein the connector molecule is specific for one of the desired molecules in the testing sample;

at least one detector molecule having an affinity for and specific for one of the desired molecule, wherein the detector molecule comprises a fluorophore label wherein the fluorophore label is positioned about 5 nm to about 40 nm from the metallic structures;

an electromagnetic energy source for exciting the fluorophore label; and a measuring device to measure emissions and determine the width of the emission spectra and color change of emissions.

Another aspect of the present invention relates to a bioassay for measuring concentration of receptor-ligand binding in a test sample, the method comprising:

a. immobilizing metallic nanostructures of the present invention on a substrate surface wherein the metallic nanostructures have positioned thereon a receptor molecule having affinity for a ligand of interest;

b. contacting the receptor molecule with the test sample suspected of comprising the ligand of interest, wherein the ligand of interest will bind to the receptor molecule to form a receptor-ligand complex;

c. contacting the receptor-ligand complex with a detector molecule having affinity for the ligand to form a receptor-ligand-detector complex, wherein the detector molecule includes a fluorophore positioned about 5 nm to about 40 nm from the metallic structures;

d. exposing the receptor-ligand-detector complex to excitation energy for excitation of the fluorophore; and e. measuring the intensity of emissions, measuring the width of emission spectrum and/or determining the color change of emissions.

The methods described above may be used in multiple detecting systems, including but not limited to, immunoassays, hybridization assays, resonance energy transfer assays, polarization/anisotropy based assays, chemiluminescence based assays, luminescence based assays, and enzyme-linked immunosorbant assays.

Other aspects and advantages of the invention will be more fully apparent from the ensuing disclosure and appended claims.

BRIEF DESCRIPTION OF THE FIGURES

(FIG. 2B) Synchronous spectra recorded for the SiOx coated slides. Note that the films are dry.

(FIG. 4B) FWHM observed for Rh800 dissolved in glycerol.

(FIG. 5B) Synchronous scattering spectra ($\lambda Ex=\lambda Em$) from both a glass slide (control sample) and Zinc coated slides (samples).

(FIG. 6B) Normalized spectra from both glass and zinc.

FIGS. 7 A and B show (FIG. 7A) Emission spectra recorded for BF aqueous solution on glass (control sample) and glass coated with a 5 nm Zn film (sample). The calculated wavelength dependence of MEF is also shown, with the mean value shown, dotted line.

(FIG. 8B) The calculated MEF magnitude and the FWHM of each Zinc thickness. G—glass control slide.

FIGS. 11 A and B show (FIG. 11A)—Fluorescence spectra of Rose Bengal measured on glass (control sample) and SiF (produced by a wet deposition technique) with an absorbance of 0.57 (sample). The MEF wavelength dependence has been calculated as a ratio of fluorescence intensities on SiFs to that on glass.

FIGS. 12 A and B show (FIG. 12A)—Fluorescence spectra of Rose Bengal measured on glass (control sample) and SiF with an absorbance of 0.67 (sample). The MEF effect has been calculated as a ratio of fluorescence intensities on SiFs to that on glass.

FIGS. 13 A and B show (FIG. 13A) Fluorescence spectra of Rose Bengal Measured on glass (control sample) and SIF with the absorbance of 1.0 (sample). The MEF effect has been calculated as a ratio of fluorescence intensities on SIFs to that on glass.

FIGS. 14 A and B show (FIG. 14A) Fluorescence spectra of Rose Bengal Measured on glass (control sample) and SIF with the absorbance of 0.48 (sample). The MEF effect has been calculated as a ratio of fluorescence intensities on SIFs to that on glass. (FIG. 14B) Normalized emission spectra from both glass and SIF. SIF-Silver Island Film.

FIGS. 15 A and B show (FIG. 15A)—Fluorescence spectra of Rose Bengal measured on glass (control sample) and SiF with the absorbance of 0.61 (sample). The MEF effect has been calculated as a ratio of fluorescence intensities on SiFs to that on glass.

FIGS. 16 A and B show (FIG. 16A)—Fluorescence spectra of Fluorescein measured on glass (control sample) and SiF with the absorbance of 0.54 (sample). The MEF effect has been calculated as a ratio of fluorescence intensities on SiFs to that on glass. (FIG. 16B)—Normalized emission spectra from both glass and SiF. SiF-Silver Island Film.

FIGS. 17 A and B shows (FIG. 17A)—Fluorescence spectra of Fluorescein measured on glass (control sample) and SiF with the absorbance of 0.67 (sample). The MEF effect has been calculated as a ratio of fluorescence intensities on SiFs to that on glass. (FIG. 17B)—Normalized emission spectra from both glass and SiF. SiF-Silver Island Film.

FIGS. 18 A and B show (FIG. 18A)—Fluorescence spectra of Fluorescein measured on glass (control sample) and SiF with the absorbance of 0.68 (sample). The MEF effect has been calculated as a ratio of fluorescence intensities on SiFs to that on glass. (FIG. 18B)—Normalized emission spectra from both glass and SiF. SiF-Silver Island Film.

DESCRIPTION OF THE INVENTION

Figure 1A:
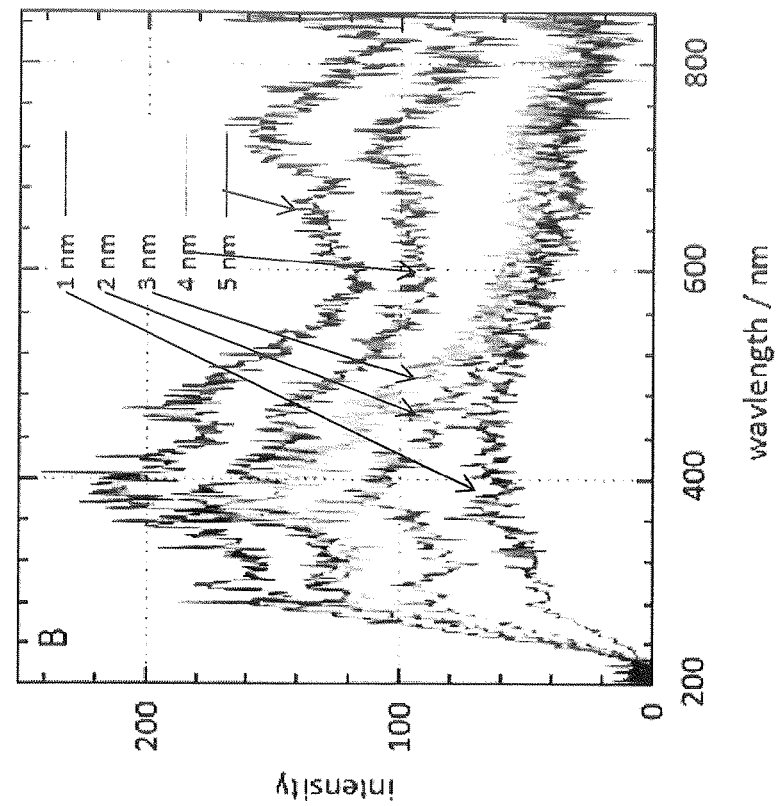
FIGS. 1 A and B show (FIG. 1A) Absorbance spectra recorded on microscopy slides coated with different thicknesses of Cu.
(FIG. 1B) Synchronous scattering spectra, $\lambda ex=\lambda em$, recorded on the Cu slides.

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl) naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 lodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivatives thereof.

Fluorophores with high radiative rates have high quantum yields and short lifetimes. Increasing the quantum yield requires decreasing the non-radiative rates k, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore distances about 5 nm to about 200 nm to metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Attaching of the fluorophore to a probe may be achieved by any of the techniques familiar to those skilled in the art. For example, the fluorophore may be covalently attached to the bimolecular probe by methods disclosed in U.S. Pat. No. 5,194,300 (Cheung) and U.S. Pat. No. 4,774,189 (Schwartz).

In another embodiment, the assay system of the present invention provides for detecting and separating at least two target pathogen by choosing fluorophores such that they possess substantially different emission spectra, preferably having emission maxima separated by greater than 10 nm, more preferably having emission maxima separated by greater than 25 nm, even more preferably separated by greater than 50 nm. When differentiation between the two fluorophores is accomplished by visual inspection, the two dyes preferably have emission wavelengths of perceptibly different colors to enhance visual discrimination. When it is desirable to differentiate between the two fluorophores using instrumental methods, a variety of filters and diffraction gratings allow the respective emission maxima to be independently detected.

Any chemiluminescent species may be used in the present invention that provides for a chemical reaction which produces a detectable reaction (observed emission) wherein the excited state responsible for the observed emission including, but not limited to the following excitation mechanisms:

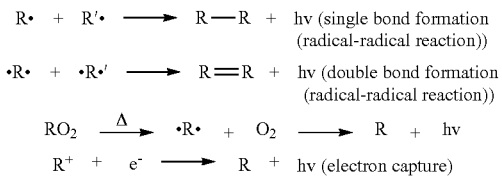

Examples of suitable chemiluminescence detector molecules include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen. Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

The present invention provides enhanced emissions using metallic structures of elliptical, spherical, triangular, rod-like forms or any geometric form. In exemplary cases, the elliptical islands have aspect ratios of 3/2, and the spherical colloids have diameters of 20-60 nm. Using known coating techniques, the placement of metallic structures could be controlled precisely, as close as 50 nm apart.

Further, the metallic structures can be fabricated to form a geometric shape such as triangle, square, oblong, elliptical, rectangle, or any shape that provides at least one apex area of the metallic surface. It is envisioned that the apex area includes not only pointed regions but regions with rounded edges such as found in an oblong or elliptical shape. The apex areas are preferably arranged so that one apex area is opposite from another apex area and aligned to cause the reactive zone to be positioned therebetween. The distances between the apex areas may range from 0.01 mm to 5 mm, more preferably from 2 mm to about 3 mm and depending on the size of the required reactive zone. The thickness of the metallic geometric shaped forms ranges from 25 nm to about 1000 nm, and more preferably from about 45 nm to about 250 nm.

The present invention further comprises a detection device for detecting emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, fluorescence correlation spectroscopy, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

Excitation light sources can include arc lamps and lasers, natural sunlight, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is beneficial for high-resolution imaging. Importantly, there is reduced background signal level gained by using 2-photon excitation as compared to 1-photon excitation by utilizing localized excitation nearby metallic particles.

In one embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, whereas microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Although fluorescence, chemiluminescence and/or bioluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 h. Thus, both the rapidity and sensitivity of small-molecule assays are still critical issues to be addressed to improve assay detection. As such the use of low intensity ultrasound will increase the rapidity of the assay.

There are many important assays that can directly benefit from enhanced signal intensities and quicker kinetics. For example, myoglobin concentrations for heart attack patients, patients of toxic shock and pancreatitis. All of these assays are widely used in hospitals emergency rooms with assay times of greater than 30 minutes. Thus, the present invention can be used for points-of-care clinical assessment in emergency rooms.

Figure 2:
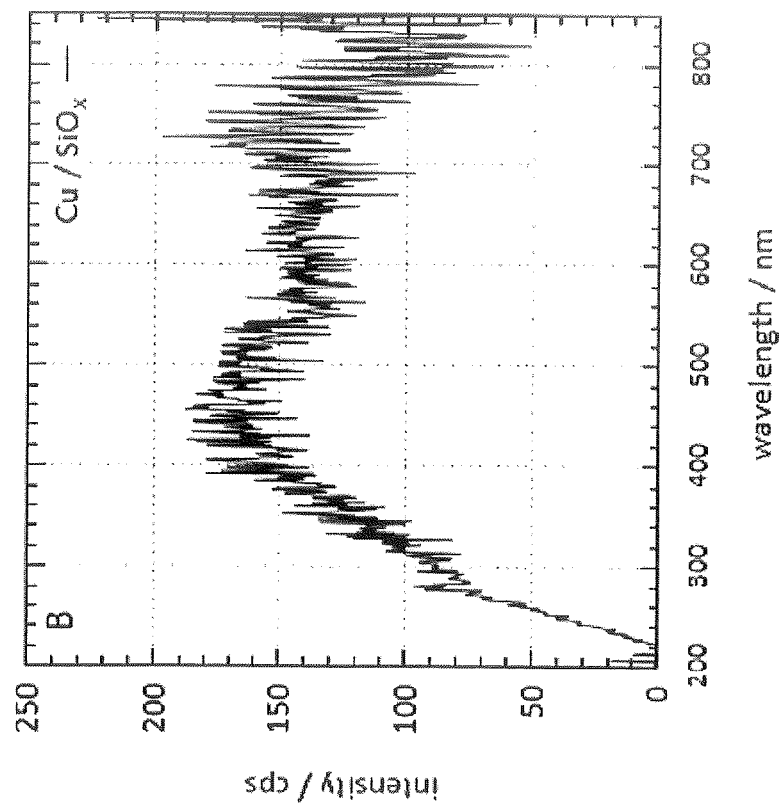
FIGS. 2 A and B show (FIG. 2A) By coating the 4 nm thick Cu films with a 4 nm layer of SiOx, it is possible to prevent oxidation of Cu. This protective coating has a large effect on the plasmon band. The absorbance and emission spectra observed for Rh800 dissolved in methanol are also shown. The chemical structure for Rh800 is shown in the inset.
Figure 2:
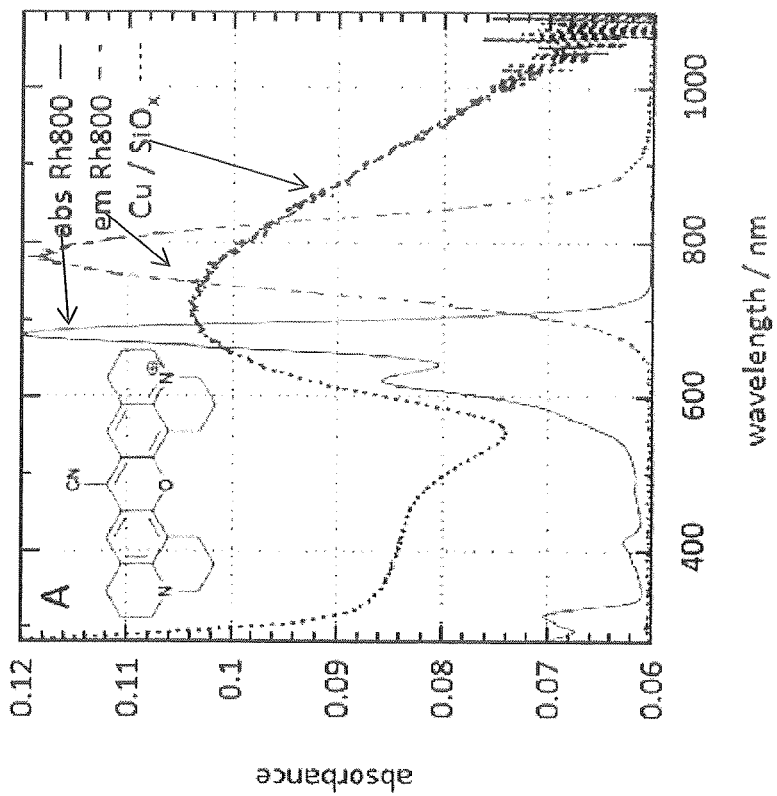

Thus it would be advantageous to increase speed of any chemical or biochemical reaction by using any device capable of generating and transmitting acoustic energy through any medium to transit ultrasonic atomizing energy. The ultrasonic emitting device can be placed in either the interior of a vessel used in a detection system or positioned adjacent thereto for transmitting energy into the vessel. The device may include components for the traditional electromagnetic stimulation of piezoelectric transducers, (manmade or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$: $R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

EXAMPLES

1. Modification of Emissions with Copper Particles

Copper films were prepared by vapor deposition under controlled conditions, i.e., by carefully controlling the deposition rate and film thickness, and such fabrication of morphologies enhanced the fluorescence signature of Rhodamine 800 (Rh 800) up to 4 times in glycerol. The enhanced fluorescence is accompanied by ≈2 nm red shift in the enhanced spectra, as compared to an otherwise identical control sample, and further, the Full Width at Half Maximum (FWHM) decreases ≈1 nm.

Rhodamine 800 and 99.995% pure copper was purchased from AnaSpec, Fremont, Calif., USA and from Research and PVD Materials Corporation, Wayne, N.J., USA, respectively. Silicon monoxide, 99.99% pure, methanol, and glycerol were purchased from Sigma-Aldrich, USA. All solvents were of spectroscopic grade. The copper was deposited at a typical rate of 0.1 nm/s on cleaned glass slides, Fisher brand, using an Edwards 360 thermal vapor deposition system equipped with a quartz crystal oscillator to monitor the rate of deposition and subsequently film thickness. The pressure in the vacuum chamber was typically $10^{-6}$ Torr.

Absorbance spectra were recorded on a Cary 50 Bio UV-Vis spectrograph, Varian, Inc. The Cu film samples were oriented perpendicular to the beam and spectra were correct for the background signal recorded from an otherwise identical but uncoated glass slide. Absorbance spectra on liquid samples were obtained using standard 1 cm quartz cuvettes. Synchronous spectra, i.e., spectra recorded when emission wavelength=excitation wavelength, were obtained on a Cary Eclipse, Varian, Inc., equipped with a plate reader. To minimize background, samples were placed on absorptive neutral density filters before mounted perpendicular to the beam in the plate reader.

Fluorescence spectra recorded from samples in standard 1 cm cuvettes were obtained on a Fluoromax 4P, Horiba, Jobin Yvone, NJ, USA. Emission spectra from samples in a sandwich configuration, i.e., from samples clamped between two $SiO_2$ slides, were recorded on a HR 2000 spectrograph from Ocean Optics. The samples were excited parallel to the surface normal using a 633 nm Helium Neon laser from JDSU, CA, USA. The excitation power was adjusted using a variable metallic neutral density filter and the power subsequently recorded on a PM100D meter equipped with a silicon photodiode sensor of model S121C from Thorlabs, USA. The excitation beam was focused on the sample using a f=50 mm lens and the emission collected front face at 45° by an optical fiber (1000 μm core diameter) with a 633 nm edge filter, Semrock, USA, placed in the beam path to block unwanted excitation light from reaching the spectrograph.

Typical absorbance and synchronous scattering spectra recorded for uncoated copper deposited on microscopy glass slides at different thicknesses are shown in FIGS. 1A and B. As is expected, the absorbance increased with film thickness, and at about 15 nm film thickness (data not shown) the absorbance becomes nearly wavelength independent indicating the formation of a continuous film. The copper Localized Resonance Plasmon Band (LRPB) is centered at ~720 nm and is most prominent at 3 nm thickness for uncoated Cu films. The distinct band below 400 nm is most likely related to excitation of inner core electrons (inter-band transitions) and will not directly contribute to the plasmon resonance band or to the MEF phenomenon. It is known that copper undergoes an oxidation reaction when exposed to atmospheric conditions and that the oxidation layer formed on the particle surface disrupts the LRPB characteristics. (21-22). To protect the Cu from oxidation, a protective layer of SiOx was deposited on top of the films. This has a profound influence on the absorbance and synchronous scattering band, as shown in FIG. 2A shows a 4 nm Cu film coated with 4 nm SiOx. Also shown in FIG. 2B are the absorption and emission spectra recorded for Rhodamine 800 dissolved in methanol. The absorbance and emission peaks are centered at 680 and 780 nm, respectively, and overlap well with the Cu LPRB band, FIG. 2B.

Figure 1B:
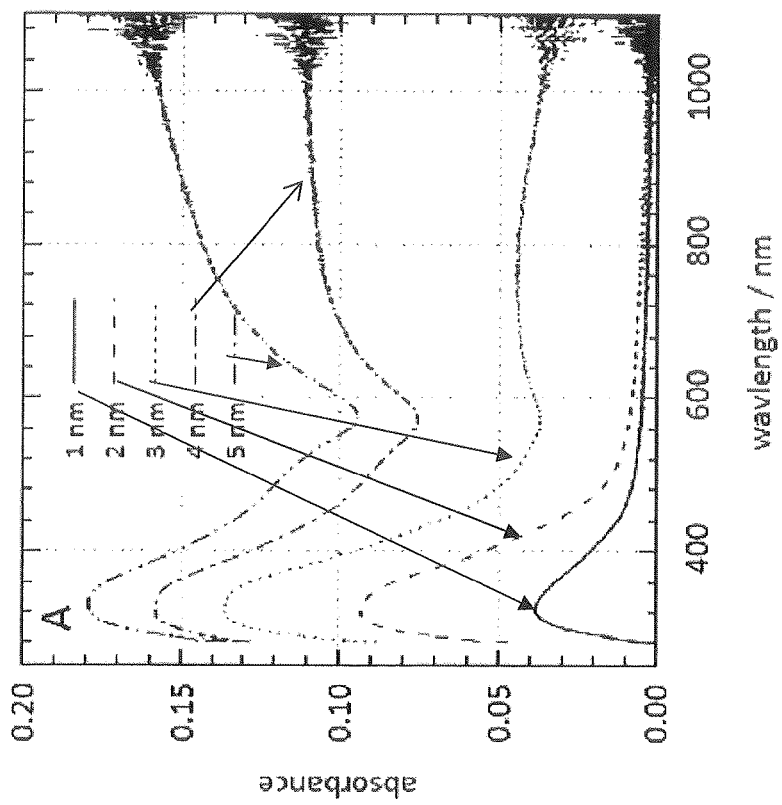

Unpolarized synchronous scattering spectra, i.e., spectra recorded on a fluorescence spectrophotometer when the wavelength setting on the excitation monochromator, $\lambda$ex, equals the wavelength setting on the emission monochromator, $\lambda$em, are shown in FIG. 1B. A detailed interpretation of the synchronous scattering spectra is very complex, since it carries convoluted information about both the absorption and scattering processes. It has however been postulated previously by Dragan et al. (23) that the synchronous scattering spectra is a good indicator of both the magnitude and the wavelength dependence of MEF, as was demonstrated by showing a correlation between the MEF spectra and the synchronous scattering spectra recorded from emissive gold clusters on silver-coated plates. The influence of the SiOx coating on the synchronous scattering spectra can also be seen from FIG. 2B. Compared with the uncoated Cu films, the signal observed from films coated with a 6 nm SiOx layer is less structured and ~10% lower in intensity. This "loss" is readily explained by the loss in Cu surface plasmons by the SiOx coating.

Figure 3:
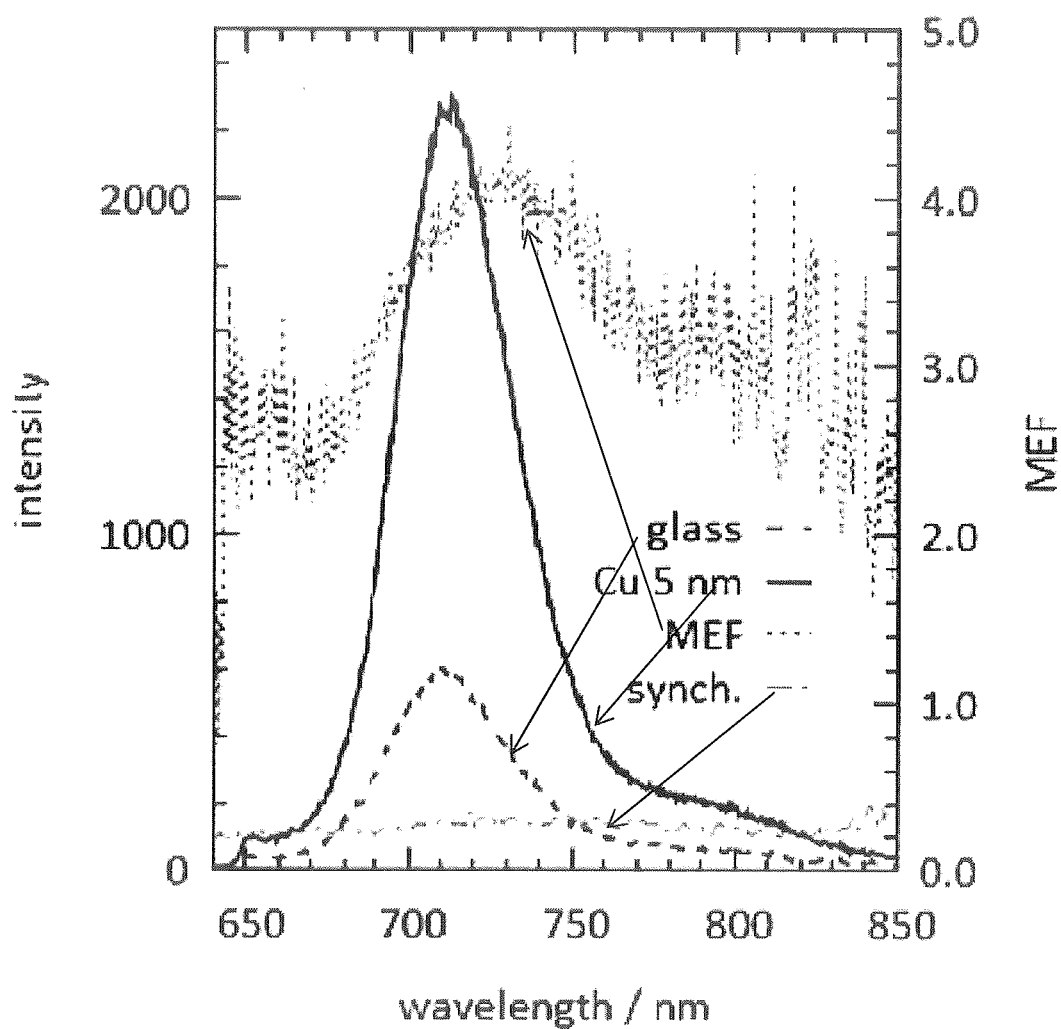
FIG. 3 shows spectra recorded for Rh800 dissolved in glycerol and sandwiched between glass slides (control) and between glass copper slides (sample). The calculated MEF response is shown together with the synchronous spectra.

The emission spectra recorded for Rh800 dissolved in glycerol and sandwiched between two glass surfaces, the reference, and between a glass and a 4 nm Cu coated slide, the sample, are shown in FIG. 3. The excitation source was a HeNe laser at 633 nm (18 mW), which overlaps well with the Cu localized plasmon resonance band. The calculated MEF spectrum obtained by dividing the sample spectrum with the reference spectrum is also shown, and most surprisingly, is non-linear. The maximum enhancement is observed close to the Rh800 emission peak, MEF ~4.1, but decreases with increasing wavelength, i.e., lower energy. It is however interesting to note that the MEF spectra are increasing on the blue side of the RH800 emission band.

Figure 4:
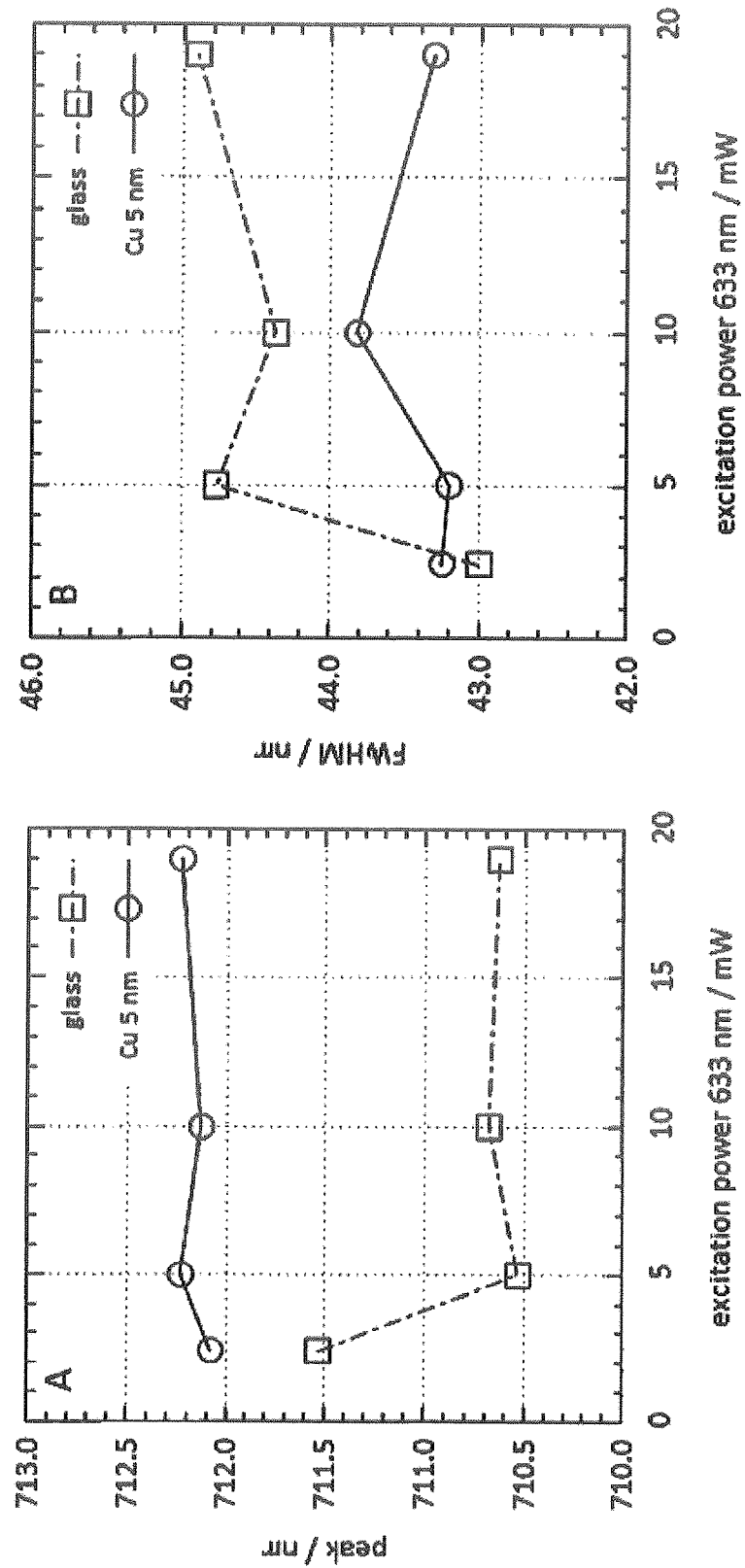
FIGS. 4 A and B show (FIG. 4A) Peak maxima observed for Rh800 dissolved in glycerol at different excitation powers. The glass sample indicates the control sample and Cu 5 nm, the sample.

The observed wavelength dependence of MEF is consequence of a ~2 nm redshift of the Rh800 emission band on the Cu substrates, as compared with the glass reference, and further by a ~1 nm reduced FWHM. The peak emission wavelength and the FWHM as functions of excitation power for Rhodamine in glycerol are shown in FIGS. 4A and 4B. In a previous report by Dragan and Geddes, (24) it was reported that metal enhanced fluorescence depends on the excitation power, explained by an power dependent effective excitation volume surrounding the fluorophores, now commonly referred to as the Excitation Volumetric Effect, EVE. A similar increase of MEF with increasing excitation power is also observed for Rh800 and further accompanied by a decrease in FWHM, FIG. 4B.

Taken together, the wavelength dependence of metal enhanced fluorescence, underpinned by a subtle red shifted emission band and narrowing of the FWHM, is strong indicatives of a much more complex interaction mechanism between the fluorophores and the localized resonance plasmon band, not hitherto reported and indeed not previously understood.

2. Modification of Emissions with Zinc Particles

The above results show spectral shifts from copper substrates with Rhodamine 800 in the red spectral region (>700 nm), but there have been no reports in the UV or visible region to date. In addition, LeRu has theoretically predicted spectral distortions, (12-13) although the fast-coupling and coupling from non-vibronically relaxed states would ultimately lead to blue-shifted emission spectra, which has not been experimentally observed to date either. Subsequently, in this testing it is shown that MEF from zinc substrates also leads to significant spectral distortion on the red edge of the spectra, with systematic changes in the enhancement factor observed, in essence, a wavelength dependence in enhancement. However, in contrast to the results in copper, the spectra observed from zinc show an increased full-width-at-half maxima (FWHM), i.e., the spectra are broader.

Basic Fuchsin and 99.995% pure zinc were purchased from Sigma-Aldrich, USA and Kurt J. Lesker Company, Material Group, Clariton, Pa., USA, respectively. Fisher brand glass slides were first washed with double dionized water and ethanol (histological grade, Fisher Scientific, USA), dried, and then plasma cleaned for 10 min. An Edwards 360 thermal vapor deposition system was used for the zinc deposition at a rate of 0.3 nm/s, under a typically pressure of $5 \times 10^{-6}$ torr. A quartz crystal oscillator was used to monitor the rate and the film thickness. A Cary 60 Bio UV-Vis spectrometer (Agilent) was used to record the absorbance spectra. Standard 4×1×1 cm cuvettes were used for Basic Fuchsin aqueous solutions, the Zinc slides were oriented perpendicular to the beam. The absorbance spectra were recorded relative to a background signal sample, uncoated glass and a cuvette filled with water, respectively.

Synchronous scattering spectra, i.e., spectra recorded when the emission wavelength=excitation wavelength ($\lambda_{Ex}=\lambda_{Em}$), were obtained on a Cary Eclipse, Varian, Inc., equipped with a plate reader. To minimize background signal, samples were placed on absorptive neutral density filters before being mounted perpendicular to the beam in the plate reader. Basic Fuchsin emission spectra were recorded using a Fluoromax 4P, Horiba, NJ, USA, in a standard 4×1×1 cm cuvette. Emission spectra of Basic Fuchsin from Zinc films of different thicknesses were recorded on a HR 2000 spectrograph from Ocean Optics. The samples were excited parallel to the surface using a 405 nm laser, Power Technology Inc, AR, USA. The excitation power was adjusted using a variable neutral density filter and the power subsequently recorded on a PM100D power meter (model S121C from Thor labs). The emission was collected through a 600 μm core diameter optic fiber from Ocean Optics, passing through a 510 nm long pass filter (Edmund Optics), removing unwanted scattered excitation light.

Figure 5:
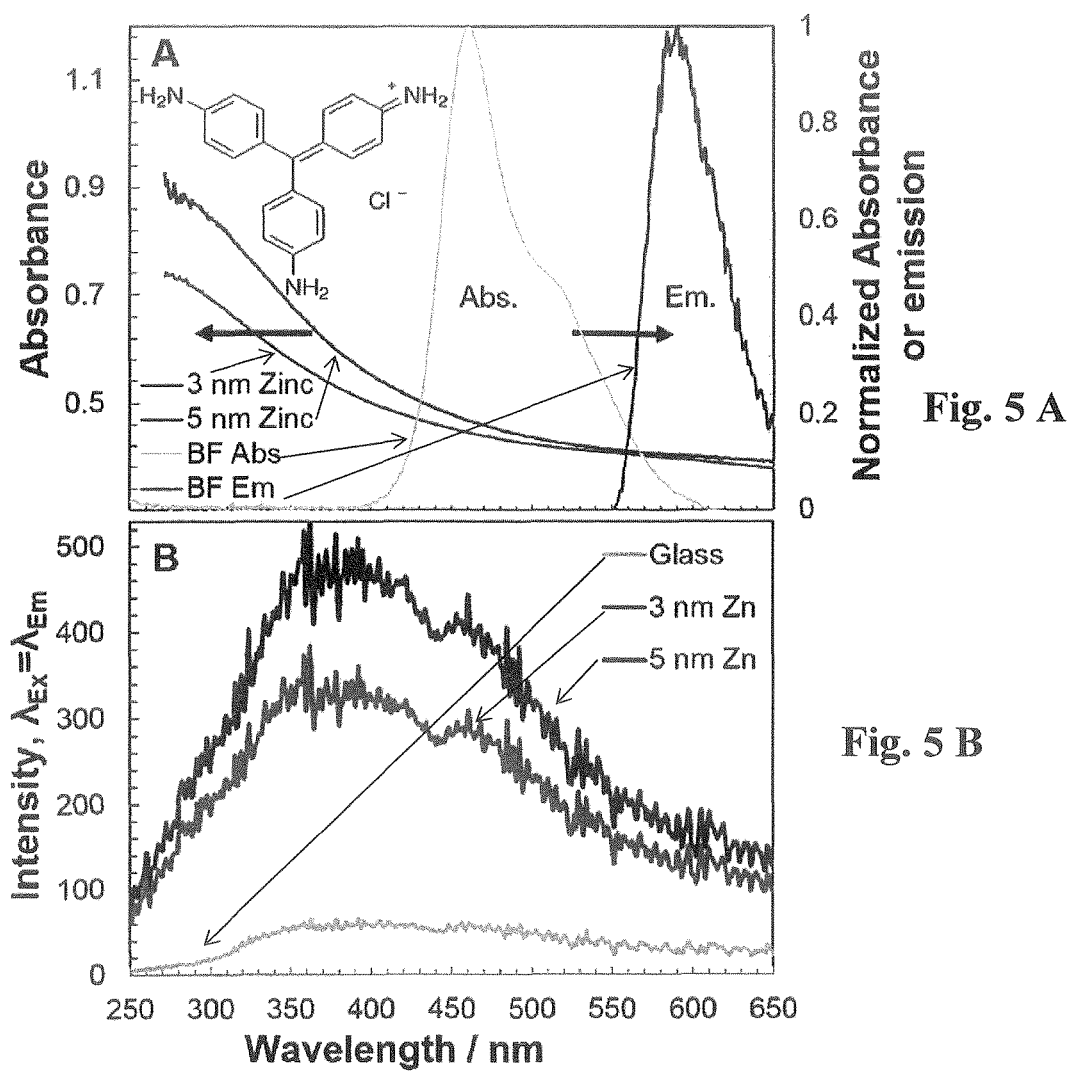
FIGS. 5 A and B show (FIG. 5A) BF aqueous solution absorbance and emission spectra. Absorbance of different Zinc thicknesses (3, 5 nm).

Zinc nanoparticulate films were deposited on glass slides, and showed a broad plasmon band, <500 nm, FIG. 5A, consistent with a previous report. (8) The unpolarized synchronous scattering spectra, i.e., when the excitation wavelength equals the emission wavelength, are shown in FIG. 5B. The synchronous scattering spectra are a convolution of both the absorption and scattering properties of the surface, and have been shown previously to be a good indicator of both the magnitude and wavelength dependence of MEF. (23) Given that large nanoparticles are dominated by the scattering portion of the extinction spectrum, i.e., scales as r (6, 25) it is clearly seen that the synchronous spectra centered ≈380, i.e., red-shifted, as compared to the absorption spectra of the zinc films in FIG. 5A. As expected, a 5 nm zinc film of particles scatter more intensely and is red-shifted as compared to a 3 nm thick zinc nanoparticulate film.

Figure 6:
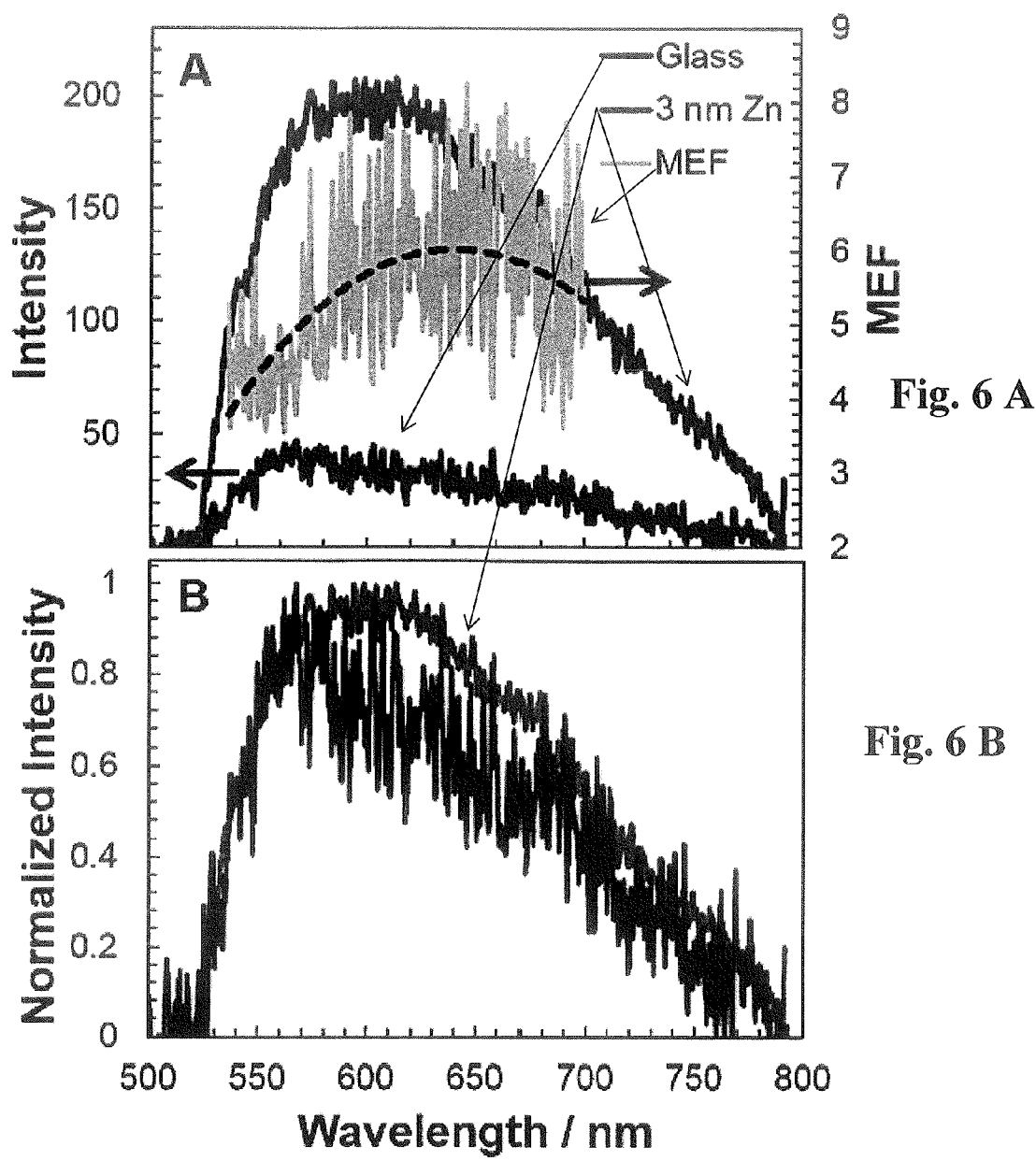
FIGS. 6 A and B show (FIG. 6A) Emission spectra recorded for BF aqueous solution on glass (control sample) and glass coated with a 3 nm Zn film (sample). The calculated MEF response is also shown, i.e., the emission response from the sample divided by the control sample, with the mean value shown, dotted line.
Figures 7A, 7B:
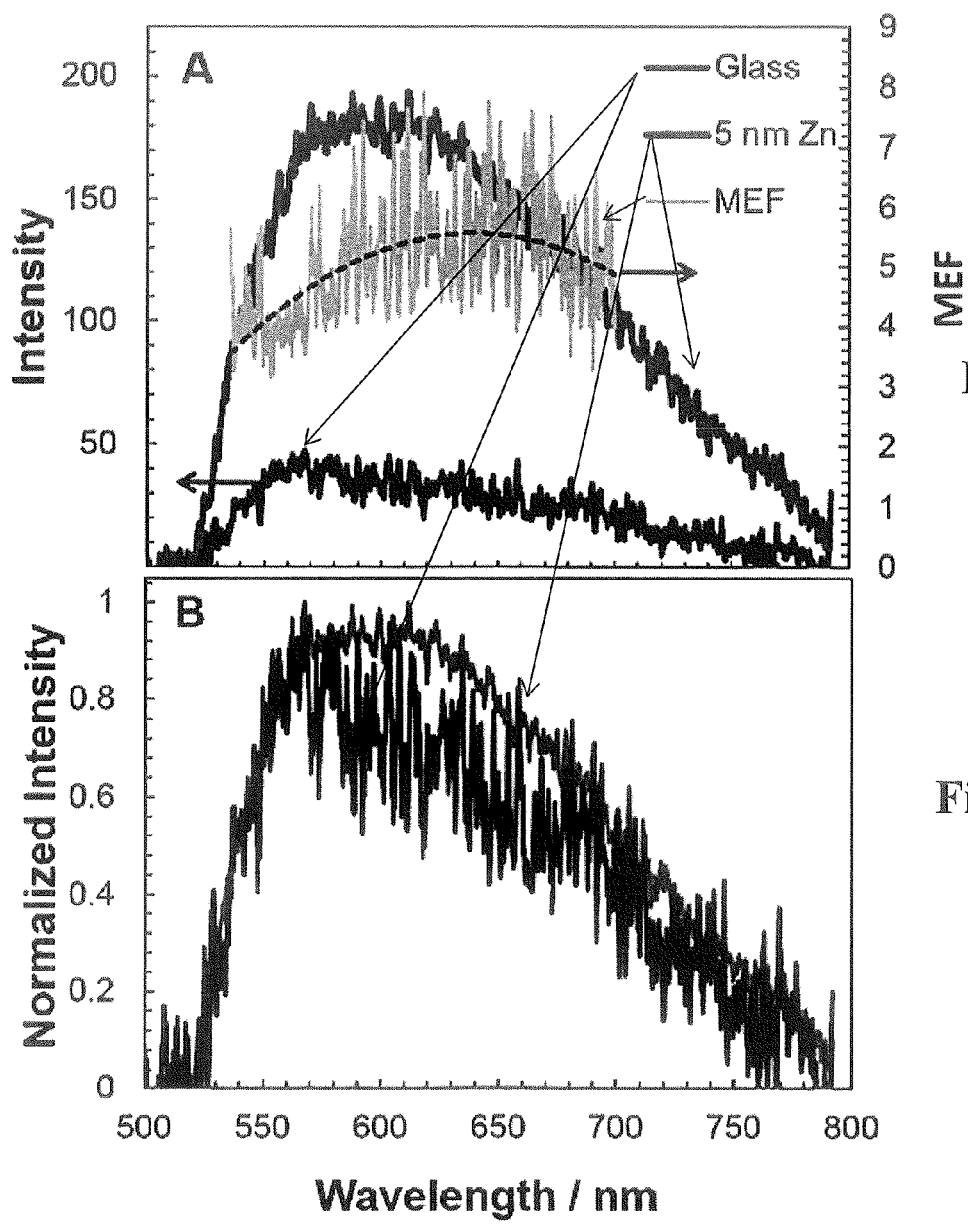
(FIG. 7B) Normalized emission spectra from both glass and zinc.

FIG. 6A shows the emission spectra of Basic Fuchsin (BF) from both a 3 nm thick zinc film and from a glass slide, a control sample which does not contain plasmon enhancing metal. Dividing these spectra, we readily generate the MEF spectra, dotted line of FIG. 6A. These MEF spectra show a wavelength dependence and have not hither to been reported for zinc. Interestingly, the MEF spectra appear to peak with a mean enhancement value 6. It is important to note that for nearly all the reports of MEF in the literature, these MEF spectra are flat, i.e., there is no wavelength dependence of enhancement observed. When the spectra are normalized, FIG. 6B, a broader metal-enhanced fluorescence BF spectrum was observed, as compared to the control sample. This is in contrast to the results above from copper substrates, where the greatest enhancements where accompanied by spectra with more reduced FWHM. Additionally, the effects of different solvents on the position of the emission spectrum were studied and it was concluded that the spectral shifts observed here are not due to a polarity effect on the fluorophore. Similar trends and results were observed for the 5 nm thick zinc nanoparticulate films, FIG. 7A and FIG. 7B.

Figure 8:
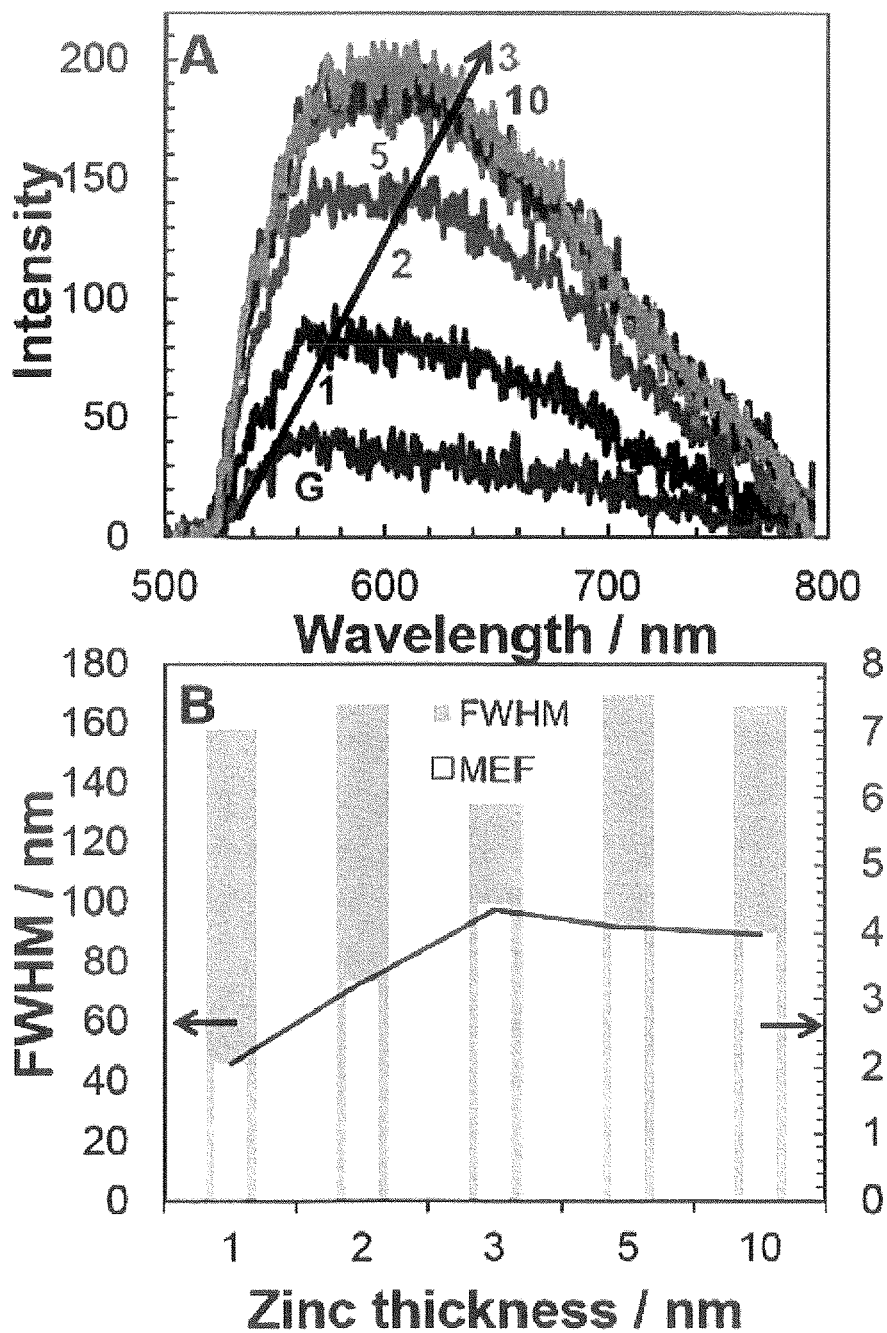
FIGS. 8 A and B show (FIG. 8A) Emission Spectra recorded for BF aqueous solution on glass (control sample) and glass coated with different thicknesses of Zinc (1, 2, 3, 5, and 10 nm).
Figure 9:
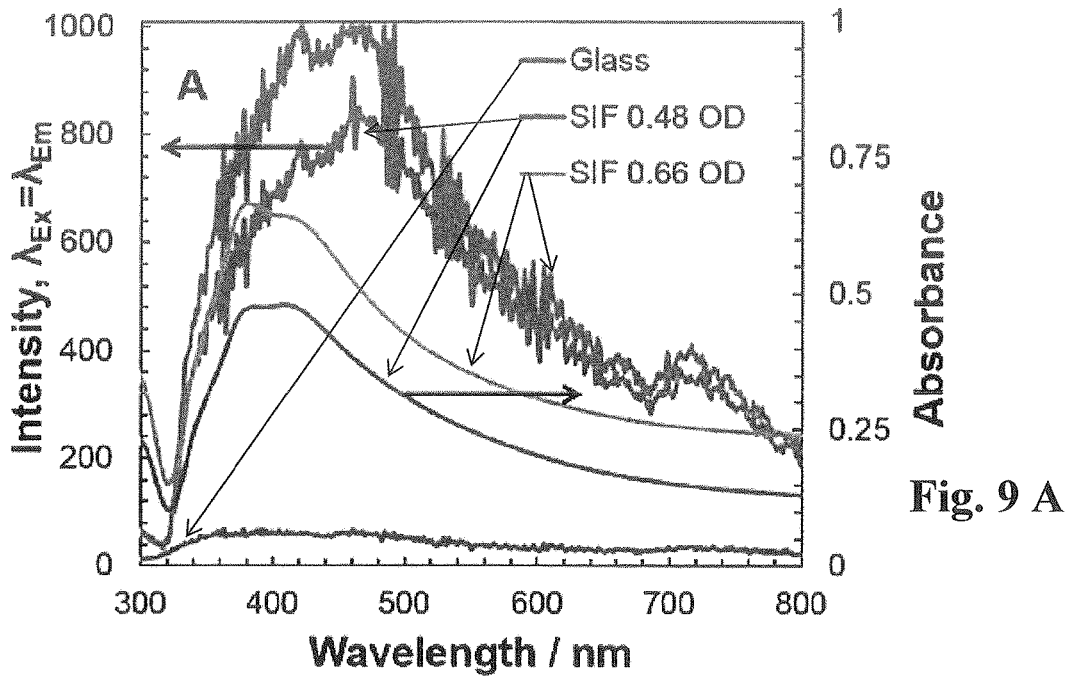
FIGS. 9 A and B show absorbance spectra and synchronous scattering spectra Intensity, ($A_{Ex}=A_{Em}$) collected from Silver Island films. The slides were obtained using a (FIG. 9A) wet and a (FIG. 9B) dry deposition. SiF-Silver Island Film.
Figure 9:
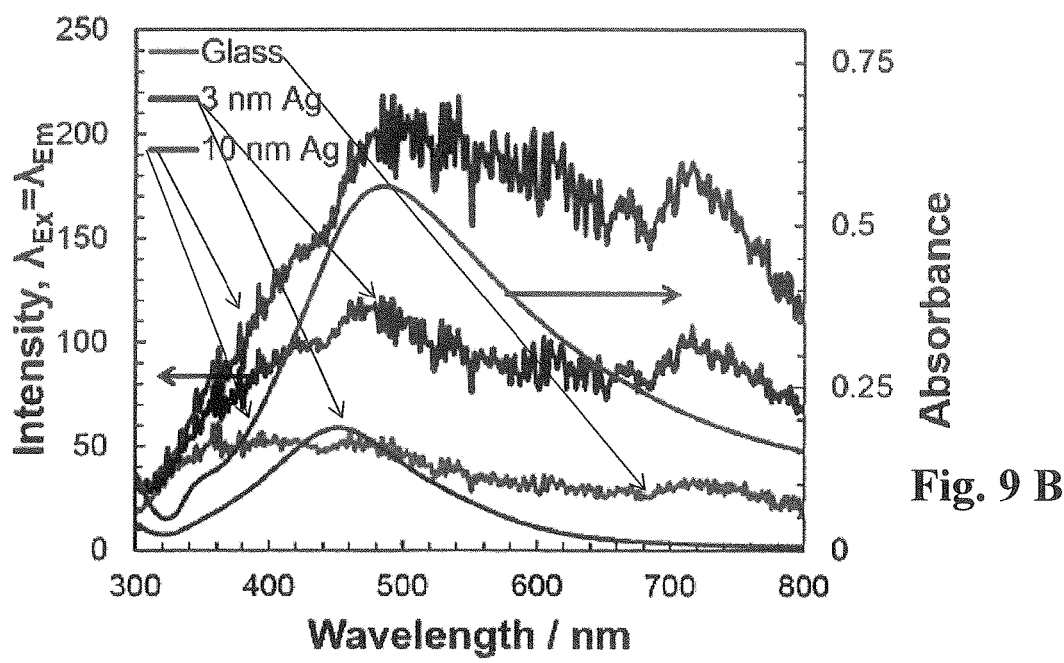

FIG. 8A shows the emission spectra from glass and the 1, 2, 3, 5, and 10 nm thick zinc films studied. As the thickness of the zinc film of particles increases, the enhancement factor (emission from zinc divided by the emission from the glass control sample) increases to a maximum enhancement for 3 nm zinc and then slightly decreases for both 5 and then 10 nm thicknesses, FIG. 8B. The FWHM remains roughly constant, except for the 3 nm thickness, i.e., the largest enhancement, which was significantly reduced, not like what was observed in the results above for copper films. At first, one may think that this result is simply experimental error. However, the spectra presented here are the mean spectra from 3 positions over the zinc surface, the results and trends being reproducible. Subsequently, similar to the previous copper example the film which provides the greatest enhancement in intensity also shows a narrower emission spectra, i.e., a reduced FWHM.

Finally, it is important to place the results of the above examples in context with the broader and current MEF thinking today. The only theoretical work to address spectral profile modifications in MEF has been undertaken by Le Ru et al., (12-13) some time back, with little experimental work being undertaken to date. Le Ru suggests that there are three possibilities for relaxation in a coupled MEF system, slow, fast, and ultrafast electron relaxation. For the slow MEF case, the excited electron relaxes to S1(0) from which it can then decay to S0. This is considered to be the standard MEF condition, similar to classical far-field fluorescence. For the fast relaxation condition, decay to the ground state, S0, may occur from any intermediate levels of S1 after absorption and the lowest level, S1(0). In Le Ru's ultra-fast MEF model, the fluorophore radiative decay rate in the presence of metal is assumed to be much faster, where no electron relaxation occurs in S1, the emission being from S1(n) to S0(n), where n is the nth vibronic level. In both the fast and ultra-fast decay models, the assumption is made that the fluorophore is both excited and that the fluorophore emits the coupled quanta itself, i.e., the metal is simply modifying the radiative decay rate of the fluorophore. Interestingly, if the fluorophore was indeed radiating/decaying faster when in close proximity to metal, then one would typically expect to see a blue shifted spectrum as compared to the control sample, which is decaying in the free space condition. This is because in classical fluorescence, the observed steady-state fluorescence spectrum is a solvent relaxed spectra. If a fluorophore is subsequently decaying quicker near-to metal, it follows that the solvent will not have had time to fully relax, and hence, a blue shifted spectrum would be expected. This effect was originally predicted by Geddes and Lakowicz in 2002 [FIG. 10 in Ref. 26], the theory being developed by Le Ru et al. in 2007, (12) but has not been experimentally verified.

However and interestingly, the experimental data to date from both copper substrates and the zinc data presented here clearly indicate a red shifted and red-edge distorted spectrum, which is not in agreement with the earlier predictions of both Geddes and Lakowicz (26) and Le Ru et al. (12) One possible explanation to this discrepancy is that in both predictions, MEF has been attributed to a metal-modified fluorophore radiative decay rate. In recent years, the present inventor has postulated a different mechanism for MEF, whereby the excited fluorophore non-radiatively transfers energy to the surface plasmons, the nanoparticle itself subsequently radiating the coupled quanta. It is therefore speculated herein whether the different plasmon energy levels, thought to be a continuum of possible states, of the nanoparticle account for the spectral distortions observed.

In conclusion, spectral distortion for a fluorophore was observed when located in the near-field close-to zinc nanoparticulate films. This spectral distortion occurs on the red-edge of the emission spectrum and accounts for the wavelength dependence of MEF. The results for zinc are not like those observed for copper films and do not appear to support the spectral profile modifications originally predicted by Geddes and Lakowicz in 2002 and theoretically by Le Ru et al. in 2007, predictions underpinned by models employing fluorophore radiative rate modifications.

3. Modification of Emissions with Silver Particles

Silver particles were deposited by two different routes. The first by a wet deposition, the second by a dry physical method, thermal vapor deposition. FIGS. 10 to 18 show spectral distortion also works for silver particles when combines with Rose Bengal, despite what method is used to deposit it on the surface (wet or dry). The results shown in FIGS. 10 to 18 show that the spectral distortion also works for classic silver, which is the typical MEF metal. The figures (as described in the legends), show spectral distortion for different thicknesses and optical density (OD) of silver on the surfaces. Optical density is typically used for the wet depositions, and both optical density (OD) and thickness (in nanometers, nm) used for the dry depositions.

Figure 10:
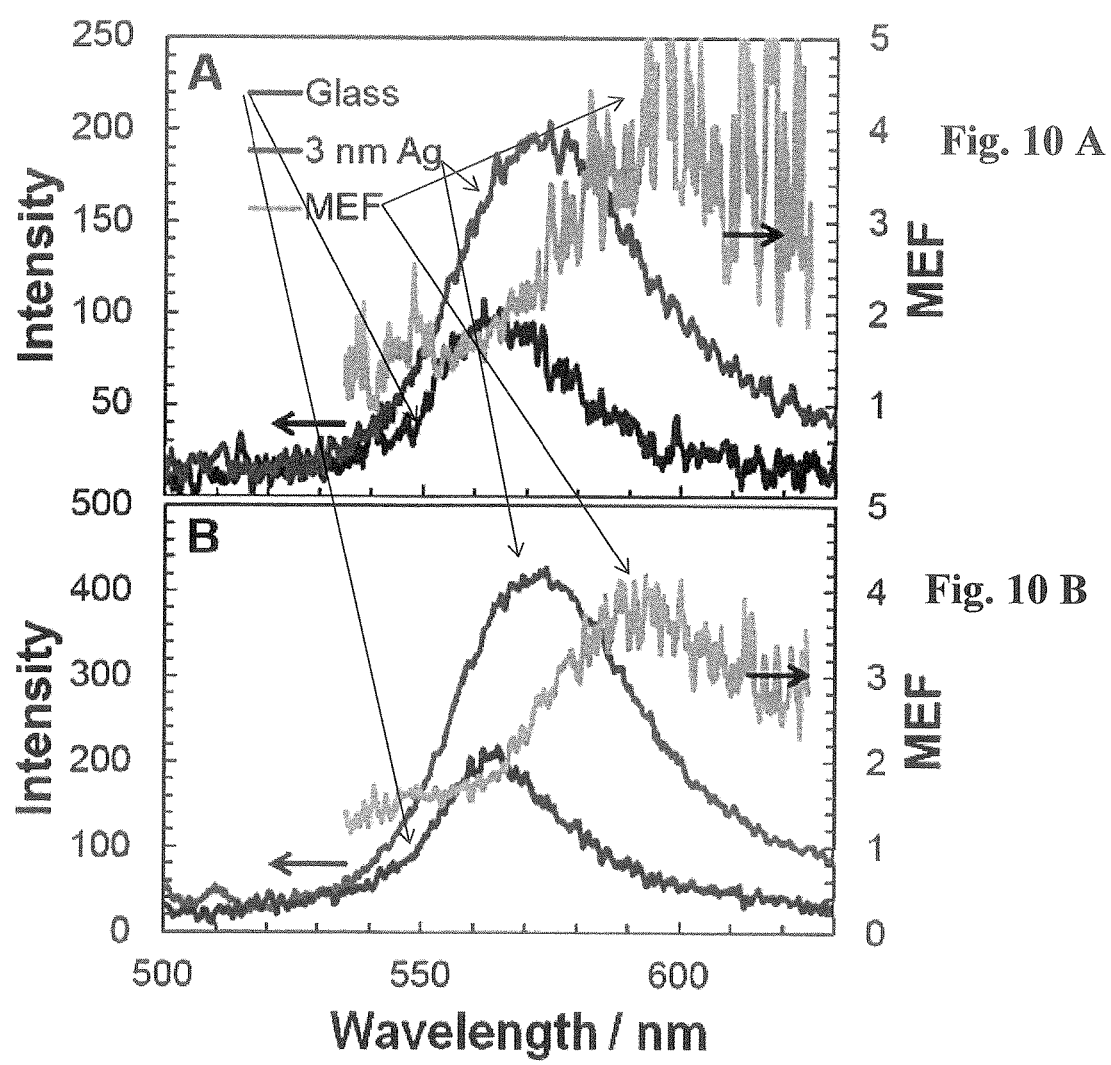
FIGS. 10 A and B show spectra recorded for Rose Bengal aqueous solution on glass (control sample) and glass coated with a 3 nm Ag film thermally evaporated (sample). Excitation was undertaken using a 473 nm CW laser line of (FIG. 10A)—10 mW and (FIG. 10B)—20 mW power. The calculated MEF response is also shown, i.e the emission response from the sample divided by the control sample.

FIGS. 10 A and B show spectra recorded for Rose Bengal aqueous solution on glass (control sample) and glass coated with a 3 nm Ag film thermally evaporated (sample). Excitation was undertaken using a 473 nm CW laser line of (FIG. 10A)—10 mW and (FIG. 10B)—20 mW power. The calculated MEF response is also shown, i.e the emission response from the sample divided by the control sample.

Figures 11A, 11B:
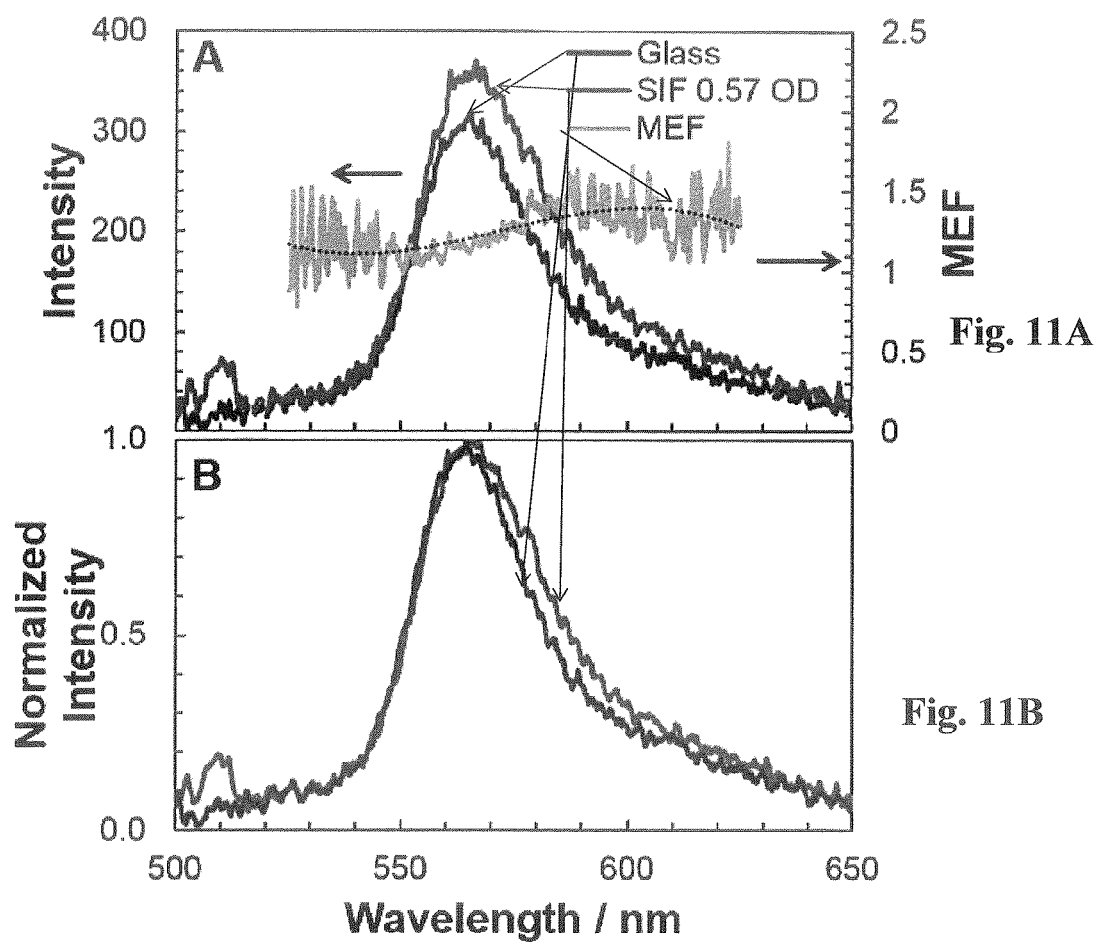
(FIG. 11B)—Normalized emission spectra from both glass and SiF. SiF-Silver Island Film.

FIGS. 11 A and B show (FIG. 11A)—Fluorescence spectra of Rose Bengal measured on glass (control sample) and SiF (produced by a wet deposition technique) with an absorbance of 0.57 (sample). The MEF wavelength dependence has been calculated as a ratio of fluorescence intensities on SiFs to that on glass. (FIG. 11B)—Normalized emission spectra from both glass and SiF. SiF-Silver Island Film.

Figures 12A, 12B:
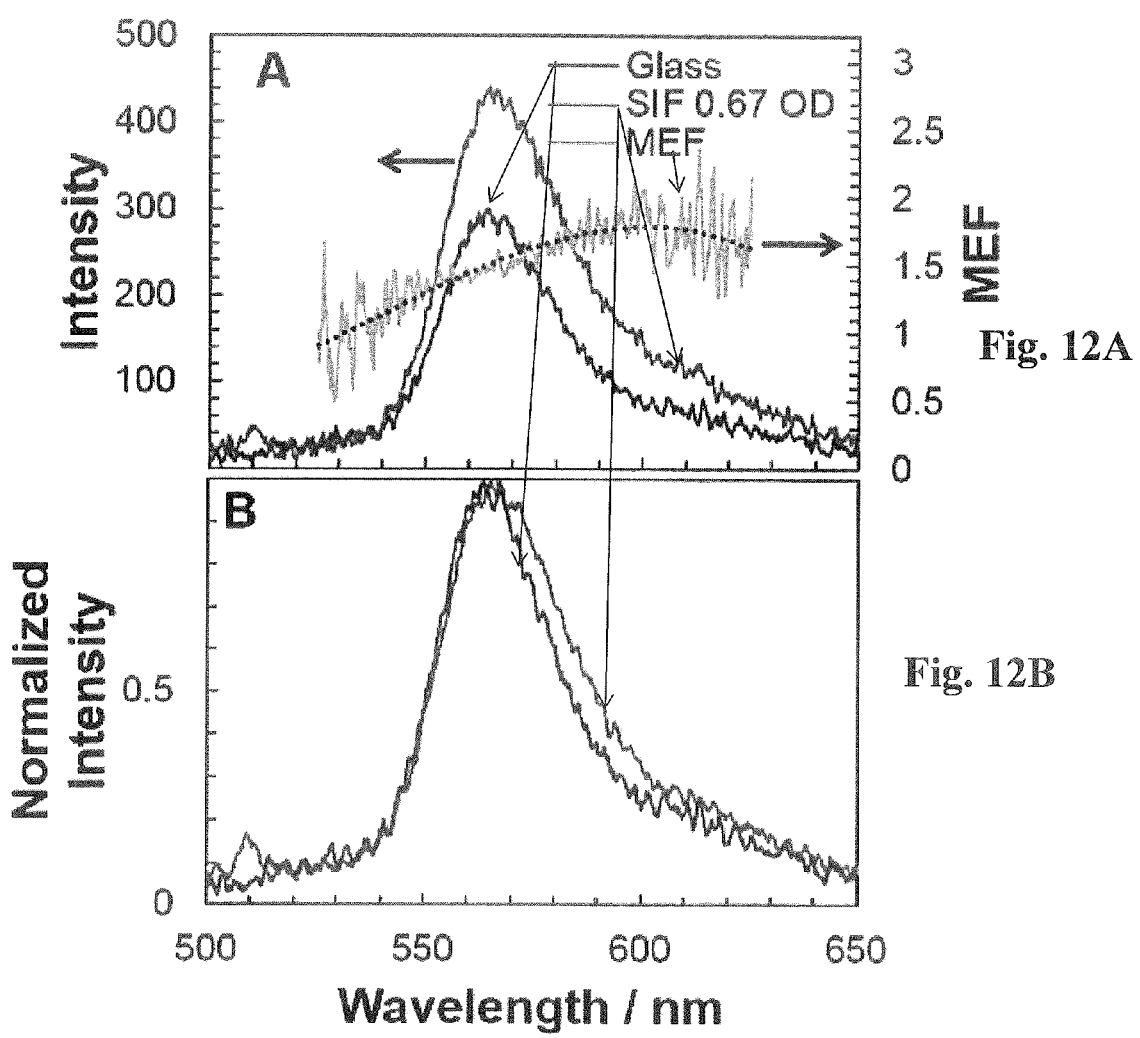
(FIG. 12B)—Normalized emission spectra from both glass and SiF. SiF-Silver Island Film.

FIGS. 12 A and B show (FIG. 12A)—Fluorescence spectra of Rose Bengal measured on glass (control sample) and SiF with an absorbance of 0.67 (sample). The MEF effect has been calculated as a ratio of fluorescence intensities on SiFs to that on glass. (FIG. 12B)—Normalized emission spectra from both glass and SiF. SiF-Silver Island Film.

Figures 13A, 13B:
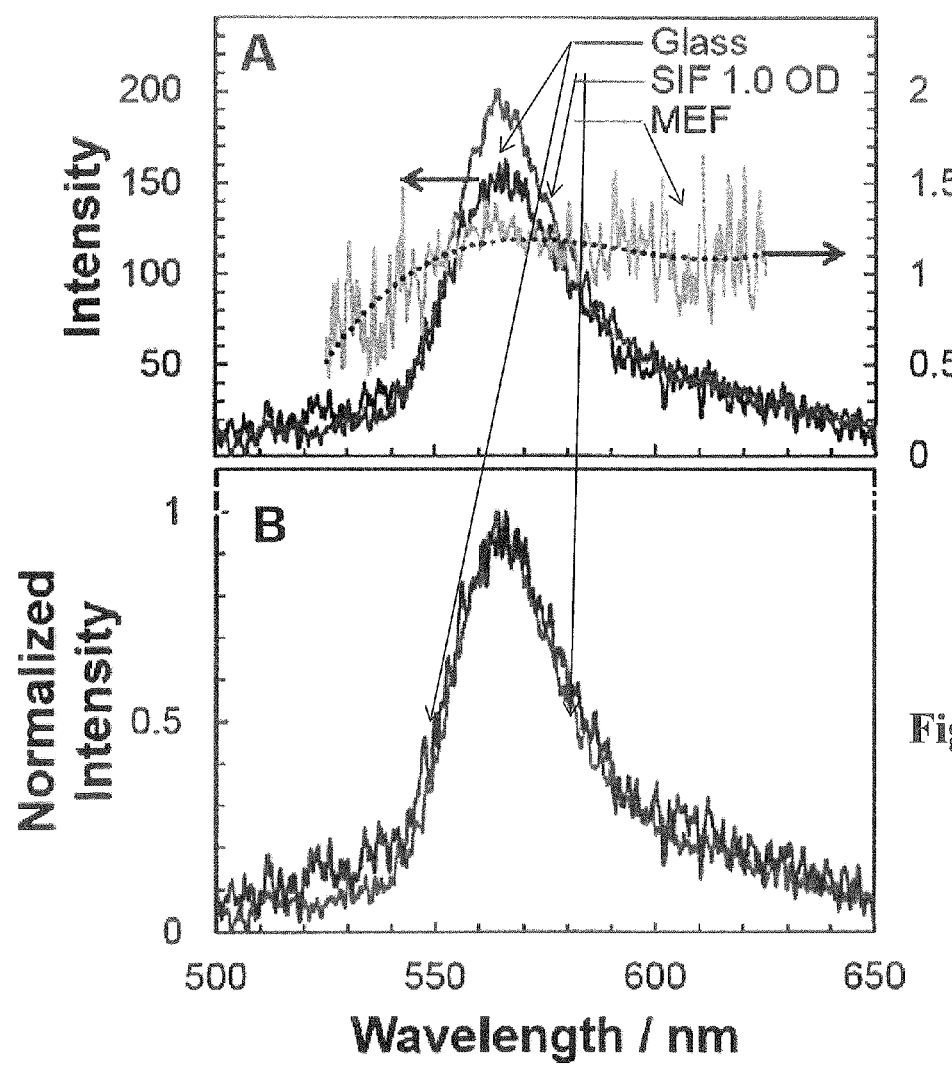
(FIG. 13B) Normalized emission spectra from both glass and SIF. SIF-Silver Island Film.

FIGS. 13 A and B show (FIG. 13A) Fluorescence spectra of Rose Bengal Measured on glass (control sample) and SIF with the absorbance of 1.0 (sample). The MEF effect has been calculated as a ratio of fluorescence intensities on SIFs to that on glass. (FIG. 13B) Normalized emission spectra from both glass and SIF. SIF-Silver Island Film.

FIGS. 14 A and B show (FIG. 14A) Fluorescence spectra of Rose Bengal Measured on glass (control sample) and SIF with the absorbance of 0.48 (sample). The MEF effect has been calculated as a ratio of fluorescence intensities on SIFs to that on glass. (FIG. 14B) Normalized emission spectra from both glass and SIF. SIF-Silver Island Film.

Figures 15A, 15B:
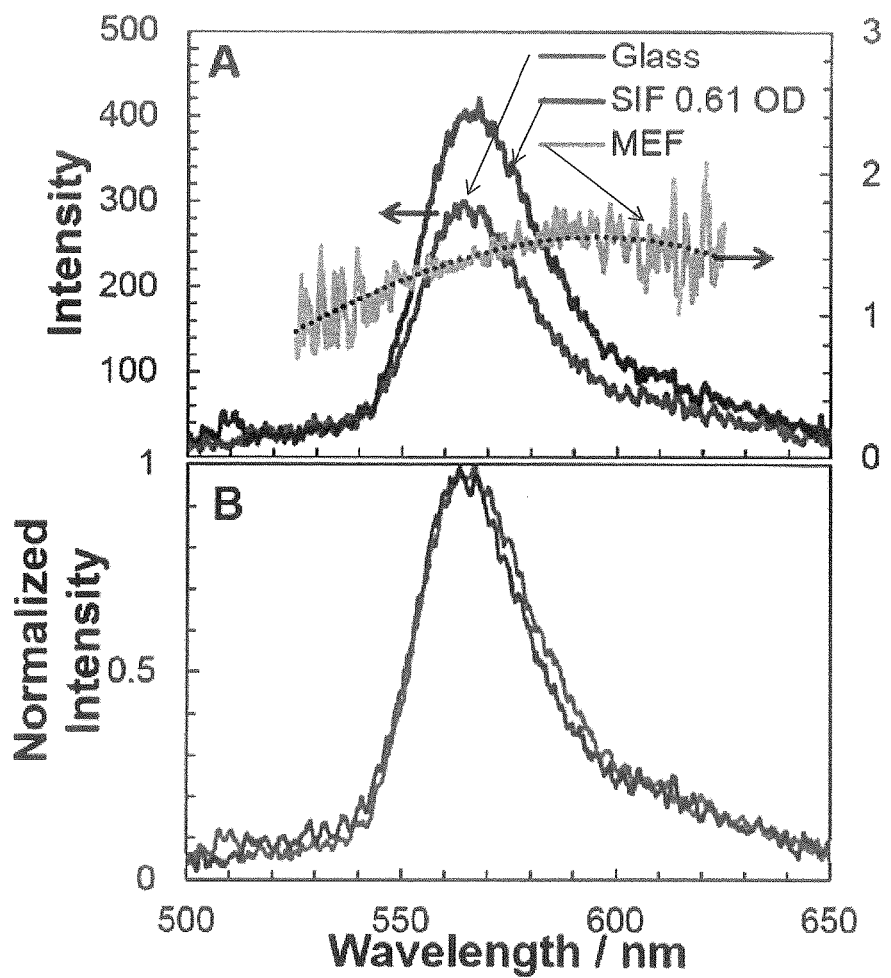
(FIG. 15B)—Normalized emission spectra from both glass and SiF. SiF-Silver Island Film.
Figure 19:
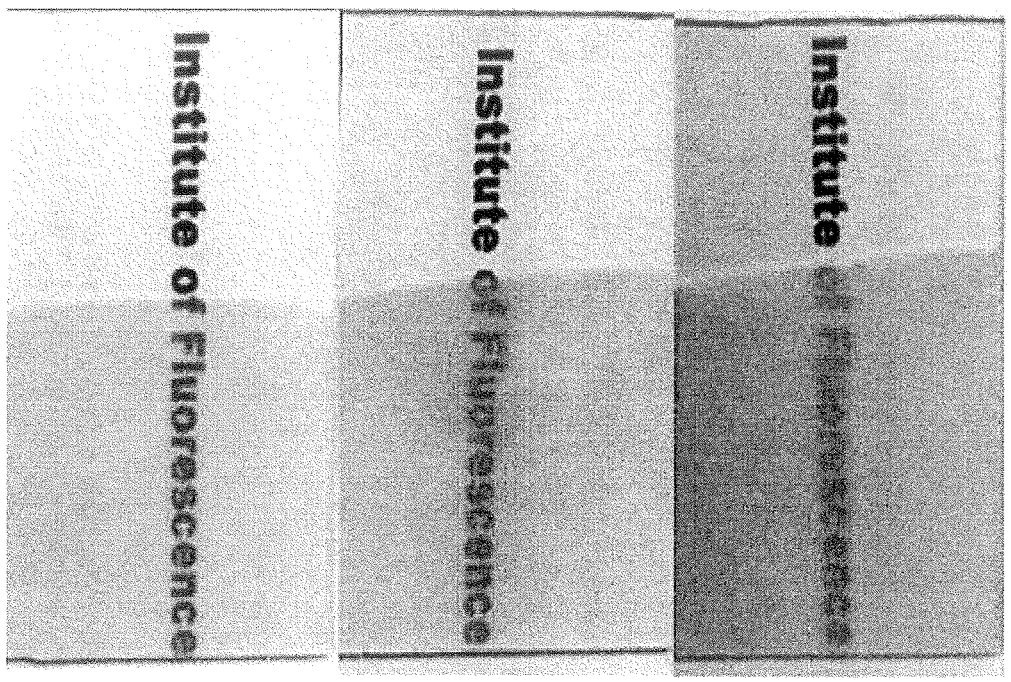
FIG. 19 shows Silver Island Film with the absorbance 0.582, 0.82 and 1.0 (left to right).

FIGS. 15 A and B show (FIG. 15A)—Fluorescence spectra of Rose Bengal measured on glass (control sample) and SiF with the absorbance of 0.61 (sample). The MEF effect has been calculated as a ratio of fluorescence intensities on SiFs to that on glass. (FIG. 15B)—Normalized emission spectra from both glass and SiF. SiF-Silver Island Film.

FIGS. 16 A and B show (FIG. 16A)—Fluorescence spectra of Fluorescein measured on glass (control sample) and SiF with the absorbance of 0.54 (sample). The MEF effect has been calculated as a ratio of fluorescence intensities on SiFs to that on glass. (FIG. 16B)—Normalized emission spectra from both glass and SiF. SiF-Silver Island Film.

FIGS. 17 A and B shows (FIG. 17A)—Fluorescence spectra of Fluorescein measured on glass (control sample) and SiF with the absorbance of 0.67 (sample). The MEF effect has been calculated as a ratio of fluorescence intensities on SiFs to that on glass. (FIG. 17B)—Normalized emission spectra from both glass and SiF. SiF-Silver Island Film.

FIGS. 18 A and B show (FIG. 18A)—Fluorescence spectra of Fluorescein measured on glass (control sample) and SiF with the absorbance of 0.68 (sample). The MEF effect has been calculated as a ratio of fluorescence intensities on SiFs to that on glass. (FIG. 18B)—Normalized emission spectra from both glass and SiF. SiF-Silver Island Film.

REFERENCES

The contents of all references cited herein are hereby incorporated by reference herein for all purposes.

C. D. Geddes, Phys. Chem. Chem. Phys. 15(45), 19537 (2013).
N. Sui, L. Wang, T. Yan, F. Liu, J. Sui, Y. Jiang, J. Wan, M. Liu, and W. W. Yu, Sens. Actuators B 202, 1148-1153 (2014).
3, M. Bauch, K. Toma, M. Toma, Q. Zhang, and J. Dostalek, Plasmonics 9(4), 781-799 (2014).
4. M. Ganguly, C. Mondal, J. Chowdhury, J. Pal, A. Pal, and T. Pal, Dalton Trans. 43(3), 1032-1047 (2014).
5. L. Zhang, Y. Song, T. Fujita, Y. Zhang, M. Chen, and T.-H. Wang, Adv. Mater. 26(8), 1289-1294 (2014).
6. Y. Zhang, K. Aslan, M. J. R. Previte, and C. D. Geddes, Appl. Phys. Lett. 90(17), 173116 (2007).
7. M. H. Chowdhury, K. Ray, S. K. Gray, J. Pond, and J. R. Lakowicz, Anal. Chem. 81(4), 1397-1403 (2009).
8. K. Aslan, M. J. R. Previte, Y. Zhang, and C. D. Geddes, J. Phys. Chem. C 112(47), 18368-18375 (2008).
9. R. Matsumoto, H. Yonemura, and S. Yamada, J. Phys. Chem. C 117(6), 2486-2493 (2013).
10. X. Zhang, L. Fu, J. Liu, Y. Kuang, L. Luo, D. G. Evans, and X. Sun, Chem. Commun. 49(34), 3513-3515 (2013).
11. J. Karolin and C. Geddes, Appl. Phys. Lett. 105(6), 063102 (2014).
12. E. C. Le Ru, P. G. Etchegoin, J. Grand, N. Félidj, J. Aubard, and G. Lévi, J. Phys. Chem. C 111(44), 16076-16079 (2007).
13. E. C. L. Ru, J. Grand, N. Félidj, J. Aubard, G. Lévi, A. Hohenau, J. R. Krenn, E. Blackie, and P. G. Etchegoin, in Metal-Enhanced Fluorescence, edited by C. D. Geddes (John Wiley & Sons, Inc., 2010), pp. 25-65.
14. A. I. Dragan and C. D. Geddes, "Metal-enhanced fluorescence: The role of quantum yield, Q(0), in enhanced fluorescence," Appl. Phys. Lett. 100, 093115 (2012).
15. C. D. Geddes, Metal-Enhanced Fluorescence (Wiley-Blackwell, Oxford, 2010).
16. C. D. Geddes and M. H. Chowdhury, "Plasmonics special issue—Advances in metal-molecular interactions," Plasmonics 2, 95 (2007).
17. N. Mauser and A. Hartschuh, "Tip-enhanced near-field optical microscopy," Chem. Soc. Rev. 43, 1248-1262
18. Y. X. Zhang, B. L. Mali, C. Aitken, and C. D. Geddes, "Highly sensitive quantitation of human serum albumin in clinical samples for hypoproteinemia using metal-enhanced fluorescence," J. Fluoresc. 23, 187-192 (2013).
19. A. I. Dragan, M. T. Albrecht, R. Pavlovic, A. M. Keane-Myers and C. D. Geddes, "Ultra-fast pg/ml anthrax toxin (protective antigen) detection assay based on microwave-accelerated metal-enhanced fluorescence," Anal. Biochem. 425, 54-61 (2012).
20. S. M. Tennant, Y. X. Zhang, J. E. Galen, C. D. Geddes, and M. M. Levine, "Ultra-fast and sensitive detection of non-typhoidal salmonella using microwave-accelerated metal-enhanced fluorescence ("MAMEF")," PLoS One 6, e18700 (2011).
21. G. H. Chan, J. Zhao, E. M. Hicks, G. C. Schatz, and R. P. Van Duyne, "Plasmonic properties of copper nanoparticles fabricated by nanosphere lithography," Nano Lett. 7, 1947-1952 (2007).
22. K. Sugawa, T. Tamura, H. Tahara, D. Yamaguchi, T. Akiyama, J. Otsuki, Y. Kusaka, N. Fukuda, and H. Ushijima, "Metal-enhanced fluorescence platforms based on plasmonic ordered copper arrays: Wavelength dependence of quenching and enhancement effects," ACS Nano 7, 9997-10010 (2013).
23. A. I. Dragan, B. Mali, and C. D. Geddes, "Wavelength-dependent metal-enhanced fluorescence using synchronous spectral analysis," Chem. Phys. Lett. 556, 168-172 (2013).
24. A. I. Dragan and C. D. Geddes, "Excitation volumetric effects (EVE) in metal-enhanced fluorescence," Phys. Chem. Chem. Phys. 13, 3831-3838 (2011).
25. K. Aslan, I. Gryczynski, J. Malicka, E. Matveeva, J. R. Lakowicz, and C. D. Geddes, Curr. Opin. Biotechnol. 16(1), 55-62 (2005).
26. C. Geddes and J. Lakowicz, J. Fluorescence 12(2), 121-129 (2002).
27. K. Aslan, Z. Leonenko, J. Lakowicz, and C. Geddes, J. Fluorescence 15(5), 643-654 (2005).

That which is claimed is:

1. A method of spectrally modifying emission spectra of an excitable molecule, the method comprising:
   providing a substrate comprising a film of metallic copper or zinc nanoparticles positioned on a surface of the substrate, wherein the film has a thickness of about 3 nm to about 5 nm;
   providing at least one excitable molecule near-field close to the film of metallic nanoparticles, wherein the excitable molecule is a fluorescent, chemiluminescent, bioluminescent, or luminescent molecule;
   providing a source of electromagnetic energy, using the electromagnetic energy to excite the excitable molecule; and
   detecting emissions from the excitable molecule and/or the film of metallic nanoparticles, wherein an emission band in the presence of the film of metallic nanoparticles is red-shifted, relative to a control lacking the film of metallic nanoparticles.

2. The method of claim 1, wherein the emissions of the at least one excitable molecule in the presence of the film of metallic nanoparticles is enhanced relative to a control lacking the film of metallic nanoparticles.

3. The method of claim 2, wherein the enhanced emissions are wavelength dependent.

4. The method of claim 3, wherein the wavelength dependency of the enhanced emissions is evidenced using synchronous scattering spectra.

5. The method of claim 1, wherein a synchronous scattering spectra of the at least one excitable molecule in the presence of the film of metallic nanoparticles has a full width at half maximum (FWHM) value that is either greater than or less than a synchronous scattering spectra of the control lacking the film of metallic nanoparticles.

6. The method of claim 1, wherein the emission spectra are distorted on the red edge in a range from 1 to 10 nm thereby causing a change in color of the emission spectra.

7. The method of claim 1, wherein the substrate comprises glass, quartz, plastic, a semiconductor, paper, cellulose, cotton, nylon, silk, sapphire, diamond, noble metal films, wool fabrics, bank notes, indium tin oxide, metallic alloys or dielectric materials.

8. The method of claim 1, wherein the method of spectrally modifying emission spectra of an excitable molecule is used to detect a target molecule in an assay selected from an immunoassay, a hybridization assay, a resonance energy transfer assay, a polarization/anisotropy based assay, a chemiluminescence based assay, a luminescence based assay or an enzyme-linked immunosorbent assay.

9. The method of claim 1, wherein the at least one excitable molecule exhibits emissions in wavelengths from UV-visible to near IR.

10. The method of claim 1, wherein the at least one excitable molecule is a fluorophore.

* * * * *